(12) United States Patent
Lambrecht et al.

(10) Patent No.: US 12,208,520 B2
(45) Date of Patent: Jan. 28, 2025

(54) DEVICES, SYSTEMS AND METHODS FOR CONTROLLING CABLE DRIVE MECHANISMS

(71) Applicant: INTUITIVE SURGICAL OPERATIONS, INC., Sunnyvale, CA (US)

(72) Inventors: Bram Gilbert Antoon Lambrecht, Redwood City, CA (US); Thomas G. Cooper, Menlo Park, CA (US); Andrew Cullen Waterbury, Santa Clara, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 18/280,874

(22) PCT Filed: Mar. 7, 2022

(86) PCT No.: PCT/US2022/019087
§ 371 (c)(1),
(2) Date: Sep. 7, 2023

(87) PCT Pub. No.: WO2022/192109
PCT Pub. Date: Sep. 15, 2022

(65) Prior Publication Data
US 2024/0149438 A1 May 9, 2024

Related U.S. Application Data

(60) Provisional application No. 63/157,858, filed on Mar. 8, 2021.

(51) Int. Cl.
*B25J 9/10* (2006.01)
*A61B 34/00* (2016.01)
(Continued)

(52) U.S. Cl.
CPC ............... *B25J 9/104* (2013.01); *A61B 34/30* (2016.02); *A61B 34/71* (2016.02); *B66D 1/74* (2013.01)

(58) Field of Classification Search
CPC .......... B25J 9/104; A61B 34/30; A61B 34/71; B66D 1/74
See application file for complete search history.

(56) References Cited

U.S. PATENT DOCUMENTS 3,545,725 A 12/1970 Chandler et al.
7,391,173 B2 6/2008 Schena
(Continued)

FOREIGN PATENT DOCUMENTS

CN 107756388 A 3/2018
EP 3485836 A2 5/2019
GB 2296481 A 7/1996

OTHER PUBLICATIONS

International Preliminary Report on Patentability for Application No. PCT/US2022/019087, mailed Sep. 21, 2023, 09 pages.
(Continued)

*Primary Examiner* — Thomas C Diaz
(74) *Attorney, Agent, or Firm* — JONES ROBB, PLLC

(57) ABSTRACT

A cable-driven device, such as a joint or instrument of a computer-assisted manipulator system, may comprise a capstan mechanism to wind/unwind cables. The capstan mechanism comprises a capstan that has a groove in an outer surface of the capstan to guide the cables, which are routed from a take-up pulley, to spool onto the capstan as the capstan rotates. A guide element is engaged with the groove. The guide element is held translationally stationary relative to the take-up pulley, while there is relative translation between the capstan and both the guide element and the take-up pulley. Thus, as the capstan rotates, the guide element engages with the groove and forces the capstan and
(Continued)

the take-up pulley to translate relative to one another. This relative translation of the capstan and the take-up pulley may prevent deviation of a take-up angle of the cable as the cable spools onto the capstan.

24 Claims, 16 Drawing Sheets

(51) Int. Cl.
*A61B 34/30* (2016.01)
*B66D 1/74* (2006.01)

(56) References Cited

U.S. PATENT DOCUMENTS

| | | |
|---|---|---|
| 7,736,254 B2 | 6/2010 | Schena |
| 8,151,661 B2 * | 4/2012 | Schena .......... A61B 34/37 242/157.1 |
| 2019/0175287 A1 | 6/2019 | Hill et al. |
| 2020/0261169 A1 | 8/2020 | Miller et al. |
| 2021/0093408 A1 | 4/2021 | Carey et al. |

OTHER PUBLICATIONS

International Search Report and Written Opinion for Application No. PCT/US2022/019087, mailed Aug. 17, 2022, 12 pages.

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

DEVICES, SYSTEMS AND METHODS FOR CONTROLLING CABLE DRIVE MECHANISMS

This application is a U.S. national stage application under 35 U.S.C. § 371 (c) of International PCT Application No. PCT/US2022/019087, filed Mar. 7, 2022, which claims the benefit of priority to U.S. Provisional Application No. 63/157,858, filed Mar. 8, 2021 and titled "DEVICES, SYSTEMS AND METHODS FOR CONTROLLING CABLE DRIVE MECHANISMS," the entire contents of each of which are incorporated by reference herein.

FIELD

Aspects of this disclosure relate generally to cable drive mechanisms, systems, and methods, for example, for use in manipulator arms and/or instruments of computer-assisted teleoperated manipulator systems. More specifically, aspects of the disclosure related to cable drive mechanisms, systems, and methods for driving motion of manipulator arms and/or instruments coupled to the manipulator arms of computer-assisted, teleoperated medical manipulator systems.

INTRODUCTION

Computer-assisted manipulator systems ("manipulator systems"), sometimes referred to as robotically assisted systems, may comprise one or more manipulators that can be operated with the assistance of an electronic controller (e.g., computer) to move and control functions of one or more instruments that can be coupled to the manipulators. The manipulators can be used to transmit a variety of forces and torques to the instruments to perform procedures, such as medical procedures or non-medical procedures (e.g. industrial procedures).

One type of manipulator system, for example, is a medical manipulator system, which may be used to perform medical procedures, such as, for example, surgical, diagnostic, or therapeutic procedures. For example, medical manipulator systems may include teleoperated surgical systems that operate at least in part with computer assistance, such as the da Vinci® Surgical Systems commercialized by Intuitive Surgical, Inc., of Sunnyvale, California. In medical manipulator systems, the instruments coupled to the manipulators may include medical instruments, such as therapeutic instruments, diagnostic instruments, surgical instruments, and/or imaging instruments. In some examples, the medical instruments may be inserted into a patient through a natural orifice or an incision. Such instruments that are remotely controlled through drive forces from a medical manipulator system may be particularly useful, for example, in performing minimally invasive surgical procedures. A minimally invasive surgical procedure may be designed to reduce the amount of tissue that is damaged during a surgical procedure, for example by decreasing the number and/or size of incisions through which medical instruments are inserted.

A manipulator arm of a manipulator system generally comprises a plurality of mechanical links connected by joints, and an instrument may be coupled to one of the links, typically a distal link of the plural links. The joints may be operable to cause the links to move (i.e., rotate and/or translate) relative to one another, imparting various degrees of freedom to the manipulator to enable the manipulator to in turn move the instrument around a worksite. The link to which the instrument is coupled (e.g., an instrument carriage) comprises drive outputs to interface with and mechanically transfer driving forces to corresponding drive inputs of the instrument to control degrees of freedom of motion and/or other functions of the instrument. One type of joint in such manipulator systems is a prismatic joint, which provides for linear translation of two links relative to one another. For example, a prismatic joint may be used to allow an instrument carriage, to which an instrument can be coupled, to translate relative to another link of the manipulator. In some medical manipulator systems, a medical instrument may be coupled to an instrument carriage, and a prismatic joint may translate the instrument carriage along an insertion axis of the medical instrument, for example to translate the coupled instrument and thereby insert an end effector of the instrument into a patient and/or to remove the end effector from the patient.

Some joints are driven by cables to cause the relative motion of the links along or about the joint. For example, a prismatic joint may be cable driven. Other types of joints, including rotational joints, may also be cable driven. In some cable driven joints, one or more cables are routed along a path using pulleys, and a cable drive system is provided to cause the cables to move along the path to drive motion of the joint. In addition, instruments of a manipulator system may also include a cable drive system to cause cables routed through a shaft of the instrument to move along a path to drive motion of a portion of the instrument (e.g., actuate a wrist, an end effector, or otherwise control a degree of freedom of movement of the instrument). The cable drive systems may comprise a capstan to move the cables along the path to drive motion. The capstan may be rotated to wind and unwind the cables around the capstan, thereby moving the cables and driving movement of the joint or other cable driven device. As a cable winds onto the capstan, the point along the length of the capstan at which the cable joins the capstan changes. In some circumstances, this can lead to the angle between the cable and the capstan changing, which may cause problems such as causing excessive wear on the cable and/or pulleys, increasing friction, causing the cable to run off of a pulley or out of a groove in the capstan, etc. In addition, the cables may incur wear from other sources and may be fatigued over time through the stress imparted by working loads, which might lead to eventual damage or failure of a cable. Accordingly, a need exists to provide cable drive systems that address issues relating to sources of wear and fatigue and/or otherwise improve performance of a cable driven joints or other cable driven devices (e.g., instruments).

SUMMARY

Example embodiments of the present disclosure may solve one or more of the above-mentioned problems and/or may demonstrate one or more of the above-mentioned desirable features. Other features and/or advantages may become apparent from the description that follows.

In accordance with at least one embodiment of the present disclosure a capstan mechanism comprises a capstan, a drive shaft, and a guide roller. The capstan comprises an outer lateral surface, and a groove spiraling helically around the outer lateral surface of the capstan. The groove is configured to receive and guide one or more cables to spool onto the capstan as the capstan rotates. The drive shaft may be a spline drive shaft that is coupled to the capstan, wherein rotation of the spline drive shaft causes rotation of the capstan, and the capstan is moveable in translation along the spline drive shaft. The guide roller is engaged with the groove, the guide roller causing the capstan to move in translation along the spline drive shaft in response to rotation of the capstan.

In accordance with at least one embodiment of the present disclosure, a manipulator system for supporting and remotely actuating instruments comprises a manipulator. The manipulator comprises a first link, an instrument carriage, and a prismatic joint coupling the instrument carriage relative to the first link. The instrument carriage is configured to support an instrument. The prismatic joint comprises a traveling capstan mechanism, one or more cables coupled to the instrument carriage, and one or more pulleys routing the cables between the instrument carriage and the traveling capstan mechanism. The traveling capstan mechanism comprises a capstan, a drive shaft, and a guide roller. The capstan comprises an outer lateral surface, and a groove spiraling helically around the outer lateral surface of the capstan. The groove is configured to receive and guide a cable to spool onto the capstan as the capstan rotates. The drive shaft is coupled to the capstan, rotation of the drive shaft causes rotation of the capstan, and the capstan is moveable in translation along the drive shaft. The guide roller is engaged with the groove, the guide roller causing the capstan to move in translation along the drive shaft in response to rotation of the capstan. The drive shaft may be a spline shaft.

In accordance with at least one embodiment of the present disclosure, an instrument comprises a shaft and an instrument transmission housing coupled to the shaft. The instrument transmission housing comprises a drive input configured to be driven by an actuator of a control mechanism, and a capstan mechanism coupled to the drive input. The capstan mechanism comprises a capstan, a drive shaft, and a guide roller. The capstan comprises an outer lateral surface, and a groove spiraling helically around the outer lateral surface of the capstan. The groove is configured to receive and guide one or more cables to spool onto the capstan as the capstan rotates. Actuation of the one or more cables drives degrees of freedom of the instrument and/or actuates a function of an end effector of the instrument. The drive shaft may be a spline drive shaft that is coupled to the capstan, wherein rotation of the spline drive shaft causes rotation of the capstan, and the capstan is moveable in translation along the spline drive shaft. The guide roller is engaged with the groove, the guide roller causing the capstan to move in translation along the spline drive shaft in response to rotation of the capstan.

BRIEF DESCRIPTION OF THE DRAWINGS

The present disclosure can be understood from the following detailed description, either alone or together with the accompanying drawings. The drawings are included to provide a further understanding of the present disclosure and are incorporated in and constitute a part of this specification. The drawings illustrate one or more embodiments of the present teachings and together with the description explain certain principles and operation. In the drawings.

DETAILED DESCRIPTION

Figure 1:
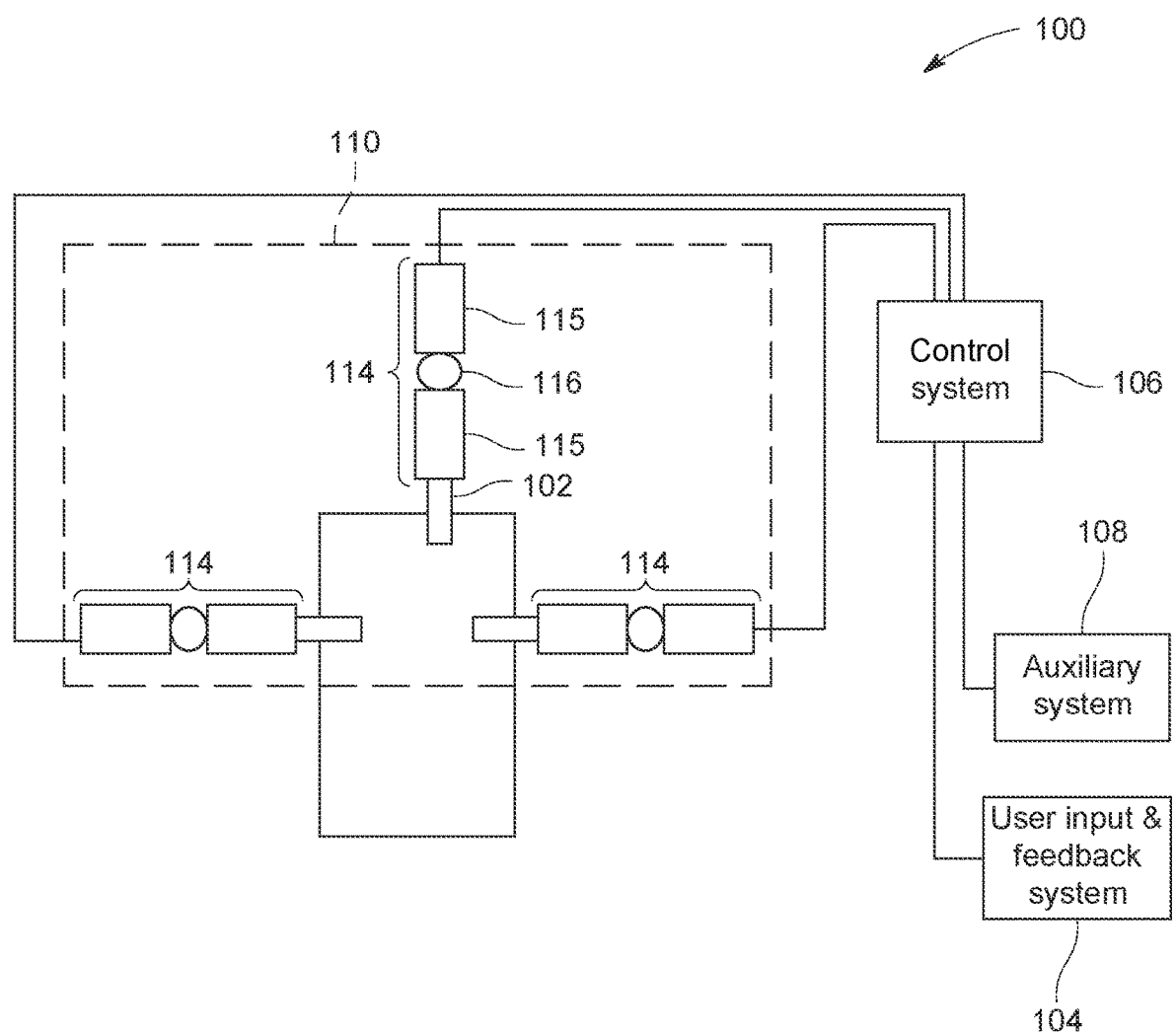
FIG. 1 is a schematic view of an embodiment of a computer-assisted manipulator system.

As noted above, cable drive systems may include one or more capstans to move cables along a path to drive motion. In a cable driven joint, the cables may be wound onto one or more capstans that are rotated to drive movement of the joint and thus movement of one element (e.g., link) relative to another element. Instruments may also include cables wound onto one or more capstans that are rotated to drive motion of a portion of the instrument (e.g., actuate an end effector or otherwise control a degree of freedom of movement). The location along the length of the capstan at which the cable winds onto (or off of) the capstan is referred to hereinafter as the "take-up location." The angle between a longitudinal axis of the capstan and the cable at the take-up location is referred to hereinafter as the "take up angle." To illustrate an example take-up location and take-up angle, reference is made to FIG. 4B, which depicts a take-up location 456 and a corresponding take-up angle θ. As mentioned above, in prior art systems, as a cable winds onto (or unwinds off from) a capstan, the take-up location will change, moving up or down an axial length of the capstan. As the capstan rotates and the take-up location changes, and if the capstan and the take-up pulley that routes the cable remain translationally fixed relative to one another, then the take-up angle will also change. For example, again considering the system illustrated in FIG. 4B, if the capstan 441 is rotated in the direction R, more of the cable 436a would wind onto the capstan 441, the take-up location 456 will move rightward (in the orientation shown in FIG. 4B) along the length of the capstan 441, and as a result take-up angle θ would increase assuming the capstan 441 and take-up pulley 442a are held translationally fixed relative to each other. The opposite would occur if the capstan 441 were rotated in the opposite direction, i.e., the cable 436a would unwind from the capstan, the take-up location 456 would move leftward, and the take-up angle θ would decrease. As the take-up angle changes, the portion of the cable extending from the capstan may move out of a preferred orientation for the cable, such as, for example, an orientation in which the cable is aligned with grooves of the capstan. This deviation of the cable from the preferred orientation may cause undesirable effects, such as causing the cables to rub against lateral walls of the pulley and capstan grooves, which may increase friction and incur additional wear. This deviation might also cause the cables to come out of the capstan grooves or cause the cables to come off of the take-up pulley. Furthermore, as the take-up angle θ changes, the cable path distance between the pulley and the capstan 441 increases. Thus, with a non-constant take-up angle, the relationship between the capstan 441 rotational angle and the location of the element whose movement is drive by the cable 436 is non-linear. The changing path length may also cause changes in the cable tension if there is no other mechanism to keep the total length of winding and unwinding cable constant. The above-described deviations of the cable from a desired orientation due to changes in the take-up angle may be referred to herein as "take-up angle deviation." The larger the take-up angle deviation is, the greater the likelihood of these undesirable effects occurring and/or the more substantial the effects may be.

One way to mitigate the above-noted issues resulting from take-up angle deviation is to move the take-up pulley radially further from the capstan. Although this does not stop the take-up angle from changing as the capstan rotates, such positioning of the take-up pulley does reduce the amount of variation in the take-up angle (i.e., the maximum take-up angle deviation is decreased), which can reduce the likelihood and/or magnitude of the undesirable effects resulting from the variation in take-up angle. However, moving the take-up pulley further from the capstan increases the amount of space taken up by the drive system, and thus this approach may be less suitable in circumstances where more compact designs are desired.

Figure 9A:
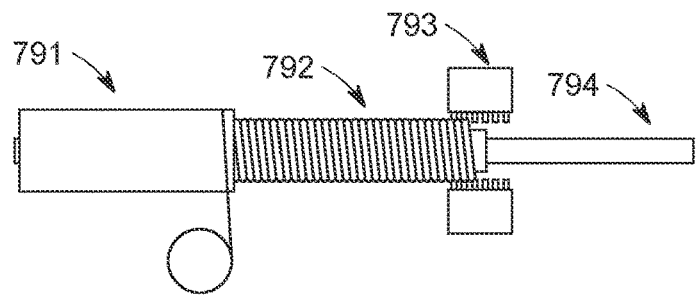
FIG. 9A-9F is a diagrammatic illustration to depict axial space requirements of a traveling capstan mechanisms in different states of operation.
Figure 9B:
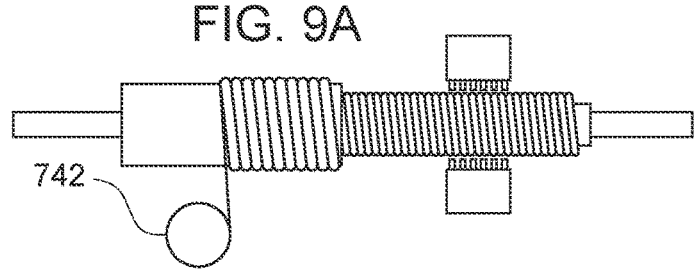
Figure 9C:
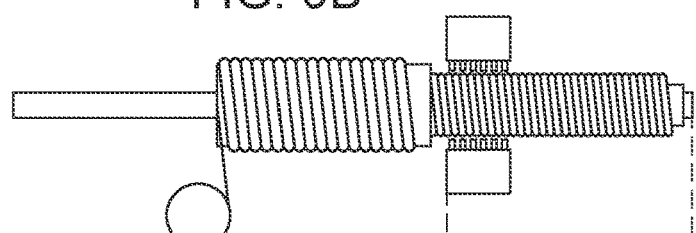

Another way to mitigate the issues associated with take-up angle deviation is to cause the capstan to move axially relative to the take-up pulley as the cable is wound onto or off from the capstan so as to counteract or eliminate the change in take-up angle. For example, as the capstan rotates, the capstan may be moved axially relative to the take-up pulley in a direction opposite the direction that the take-up location changes relative to the capstan. If the distance that the capstan is moved per rotation is matched to the distance that the take-up location moves per rotation, then the take-up location will remain stationary relative to the take-up pulley as the capstan rotates and therefore the take-up angle will remain constant. A capstan configured to translate in this manner will be referred to as a "traveling capstan." One approach to implementing such a traveling capstan is depicted in FIG. 9A-9C in which a threaded hub 792 is attached to the capstan 791 around the drive shaft 794 of the capstan, and the capstan 791 and attached threaded hub 792 are attached to the drive shaft 794 in such a way that the capstan 791 and the threaded hub 792 can translate along the drive shaft 794. The drive shaft 794 and the threaded hub 792 are passed through a threaded passageway 793 of a support structure (which is stationary relative to a take-up pulley), and the threads of the threaded hub 792 are enmeshed with the threads of the threaded passageway 793. Thus, as the capstan 791 rotates, the threaded hub 792 also rotates and its threads engage the threads of the threaded passageway 793 to force the hub 792 to translate along the drive shaft 794 (alternatively, the passageway 793 could be affixed to the capstan 701 and the threaded hub 792 could be stationary). By controlling the pitch of the threads in the hub 792 and passageway 793, the distance that the capstan 791 translates along the shaft 794 per unit of rotation may be set to match the amount by which the take-up location of the cable would tend to change per unit of rotation, thus keeping the take up-angle of the cable substantially constant as the capstan rotates. However, although this approach is effective at reducing or even eliminating the issues associated with the variation in take-up angle, there may be some drawbacks with this approach under certain circumstances.

A potential issue that may arise with such a traveling capstan is that the engagement of the threaded hub with the threaded passageway as the drive shaft rotates generates additional friction that can resist the rotation of the shaft. This increased friction may increase the amount of power needed to drive rotation, increase the amount of heat generated, increase wear on parts over time, and/or decrease power efficiency of the drive element (e.g., motor) driving the shaft. The increased friction may also require, in some circumstances, a larger and/or more costly drive element (e.g., motor) to drive the rotation. Another potential issue that may arise with such a traveling capstan is that the capstan assembly is relatively large in size (e.g., in length), due to addition of the threaded hub. In particular, the threaded hub may need to be long enough to provide a desired range of translational for the capstan, and thus in some cases may need to be as long as the portion of the capstan upon which the cables are wound, so that the hub is able to maintain engagement with the threaded passageway throughout a full length of travel of the capstan. Thus, the amount of space needed in an axial direction to allow the capstan and attached hub assembly to translate may be relatively large. Thus, using a traveling capstan approach to maintain a constant take-up angle might be less suitable in certain circumstances where a more compact design is desired.

To address these issues, certain embodiments disclosed herein may provide improved traveling capstan mechanisms, which may be used, for example, in cable drive systems of cable driven devices. Such cable driven devices may include a cable-driven joint of a robotically-assisted manipulator system or an instrument or an end effector of a manipulator system. However, the traveling capstan mechanisms disclosed herein are not limited thereto or thereby and may be used in other types of cable driven devices. The embodiments disclosed herein may reduce, mitigate, or even eliminate the problems noted above connected to take-up angle deviation. Furthermore, various embodiments disclosed herein address the problems associated with take-up angle deviation, while also addressing some of the issues noted above in relation to other approaches. Specifically, various embodiments provide a relatively compact design of a cable-driven, while exhibiting a relatively low amount of friction, as explained in greater detail below.

In accordance with certain embodiments, an improved traveling capstan mechanism may utilize a constraint mechanism that comprises a guide element that engages with the capstan to cause translation of the capstan along a drive shaft of the capstan as the capstan rotates. For example, in various embodiments a guide element engages with a cable spooling groove of the capstan and, as the capstan rotates, the guide element pushes against the lateral surfaces of the groove, forcing the capstan to translate along the drive shaft. The cable spooling groove is a groove spiraling helically around and along an outer lateral surface (radially outward facing surface) of the capstan, and is configured to receive a cable to spool the cable onto the capstan as the capstan rotates. Because the guide element follows the same grooves that the cables are wound onto, the distance the capstan is forced to translate per rotation will automatically match the distance by which the take-up point of the cable changes per rotation. Thus, deviation of the take-up angle may be eliminated.

The traveling capstan mechanisms disclosed herein may be made relatively compact, especially when compared to the first and second approaches described above. In particular, in some embodiments, the guide element may fit into an envelope of space that is the same as, or only slightly larger than, the envelope of space that would already need to be allocated for the drive system.

Moreover, various embodiments disclosed herein allow the capstan to translate along its full range of motion without significantly increasing the overall length of capstan mechanism. Thus, example embodiments disclosed herein may require less space along an axial direction than other traveling capstans, such as, for example, the traveling capstan and hub arrangement described above with reference to FIG. 9A-C. Such a space-saving comparison is discussed further below with reference to the embodiment of FIGS. 9A-9F.

In addition, in various embodiments of traveling capstan mechanisms disclosed herein, friction of various components can be maintained relatively low. Relatively low friction can be achieved by employing mechanisms that provide relative rotation between contacting surfaces and reducing the amount of sliding friction between contacting surfaces, as will be further explained with reference to the figures below.

As noted above, too large of take-up angle deviation can cause undesirable wear on the cables. However, even if take-up angle deviation is eliminated, the cables will inevitably still experience some wear and fatigue over time. To provide a more robust cable driven prismatic joint, various embodiments use a backup cable approach. Providing such a backup cable can allow the overall prismatic joint to maintain operation in the event that the corresponding primary cable is damaged, permitting uninterrupted, normal operation of the manipulator system. Further, use of the backup cables may increase safety of the device and prevent the mechanism driven by the cables from inadvertent and undesired movement in the event of primary cable failure. Moreover, use of backup cables can increase the time between maintenance of the system. In addition, when two or more cables are used, their diameters may be made smaller than if just one cable were used, as the combined strength of the smaller diameter cables may equal that of the larger diameter cable. Furthermore, using smaller diameter cables can reduce the bending stress experienced by the cables as they are wrapped around pulleys and the capstan. The backup cables may be routed alongside the primary cables and may be wound onto the same capstan as the primary cables, ensuring a seamless transition from primary to backup cable in the event of failure of the primary cable. Further, in some embodiments, the primary cables and the backup cables may share the load forces of the system equally, and thus be subjected to similar stress forces during usage of the system.

However, because the primary cables and backup cables are subjected to similar forces during usage of the system, the primary and backup cables may both be prone to experience the same amount of wear and fatigue over a period of time.

To address this, some embodiments disclosed herein may provide a cable driven prismatic joint that comprises primary cables and backup cables that experience differing stress when subjected to the same forces. Various embodiments thus contemplate backup cables that are configured to experience less stress than the primary cables during usage and when otherwise subjected to similar use and forces. One embodiment for such a backup cable utilizes a spring coupled in series with the backup cable. Another embodiment utilizes a material for the backup cable that has a lower elastic modulus than the material used for the primary cable. A combination of these two could also be employed.

Providing backup cables that are configured to experience less stress than the primary cable, the backup cables can remain less fatigued than the primary cables over the same period of usage, thus serving their intended purpose in the event the corresponding primary cable were to become damaged and cease to function properly.

As used herein and in the claims, the term computer-assisted manipulator system ("manipulator system") should be understood to refer broadly to any system comprising one or more controllable kinematic structures ("manipulators") comprising one or more links coupled together by one or more joints that can be operated to cause the kinematic structure to move. Such systems may occasionally be referred to in the art and in common usage as robotically assisted systems. The manipulators may have an instrument permanently or removably mounted thereto and may move and operate the instrument. The joints may be driven by drive elements, which may utilize any convenient form of motive power, such as but not limited to electric motors, hydraulic actuators, servomotors, etc. The operation of the manipulator may be controlled by a user (for example through teleoperation), by a computer automatically (so-called autonomous control), or by some combination of these. In examples in which a user controls at least some of the operations of the manipulator, an electronic controller (e.g., a computer) may facilitate or assist in the operation. For example, the electronic controller may "assist" a user-controlled operation by converting control inputs received from the user into electrical signals that actuate drive elements to operate the manipulators, providing feedback to the user, enforcing safety limits, and so on. The term "computer" as used in "computer-assisted manipulator systems" refers broadly to any electronic control device for controlling, or assisting a user in controlling, operations of the manipulator, and is not intended to be limited to things formally defined as or colloquially referred to as "computers." For example, the electronic control device in a computer-assisted manipulator system could range from a traditional "computer" (e.g., a general-purpose processor plus memory storing instructions for the processor to execute) to a low-level dedicated hardware device (analog or digital) such as a discrete logic circuit or application specific integrated circuit (ASIC), or anything in between. Further, manipulator systems may be implemented in a variety of contexts to perform a variety of procedures, both medical and non-medical. Thus, although some examples described in greater detail herein may be focused on a medical context, the devices and principles described herein are also applicable to other contexts, such as industrial manipulator systems.

Turning now to the figures, various example embodiments will be described in greater detail.

FIG. 1 illustrates an embodiment of a manipulator system 100. The manipulator system 100 comprises a manipulator assembly 110, a control system 106, and a user input and feedback system 104. The manipulator system 100 may also include an auxiliary system 108. These components of the manipulator system 100 are described in greater detail blow.

The manipulator assembly 110 may comprise one or more manipulators 114. FIG. 1 illustrates three manipulators 114, but any number of manipulators 114 may be included in a manipulator system 100. Each manipulator 114 comprises a kinematic structure of two or more links 115 coupled together by one or more joints 116. The joints 116 may impart various degrees of freedom of movement to the manipulator 114, allowing the manipulator 114 to be moved around a workspace. For example, some joints 116 may provide for rotation of links 115 relative to one another, other joints 116 may provide for translation of links 115 relative to one another, and so on. Some or all of the joints 116 may be powered joints, meaning a powered drive element may control movement of the joint 116 through the supply of motive power. Such drive elements may comprise, for example, electric motors, pneumatic or hydraulic actuators, etc. Additional joints 116 may be unpowered joints. In addition to drive elements that control the joints 116, the manipulator 114 may also include drive elements (not illustrated) that drive inputs of the instrument 102 to control operations of the instrument, such as moving an end-effector of the instrument, opening/closing jaws, delivering flux (e.g., electricity), etc. FIG. 1 illustrates each manipulator 114 as having two links 115 and one joint 116, but in practice a manipulator may include more links 115 and more joints 116, depending on the needs of the system 100. The more links 115 and joints 116 are included, the greater the degrees of freedom of movement of the manipulator 114.

Each manipulator 114 may be configured to support and/or operate one or more instruments 102. In some examples the instruments 102 may be fixedly coupled to the manipulator 114, while in other examples one of the links 115 may be configured to have one or more separate instruments 102 removably coupled thereto. The instruments 102 may include any tool or instrument, including for example industrial instruments and medical instruments (e.g., surgical instruments, imaging instruments, diagnostic instruments, therapeutic instruments, etc.).

The user input and feedback system 104 may include input devices to allow a user to input control commands to control operations of the manipulator system 100. Such input devices could include, for example, telepresence input devices, buttons, switches, pedals, joysticks, trackballs, data gloves, trigger-guns, gaze detection devices, voice recognition devices, body motion or presence sensors, or any other type of device for registering user input. In some examples, a telepresence input device may be provided with the same degrees of freedom as the associated instrument that they control, and as the input device is moved by a user the instrument is controlled to follow or mimic the movement of the input device, which may provide the user a sense of directly controlling the instrument. Telepresence input devices may provide the operator with telepresence, meaning the perception that the input devices are integral with the instrument. The user input and feedback system 104 may also include feedback devices, such as a display device to display images (e.g., images of the worksite as captured by one of the instruments 102), haptic feedback devices, audio feedback devices, etc.

The control system 106 may control operations of the manipulator system 100. In particular, the control system 106 may send control signals (e.g., electrical signals) to the manipulator assembly 110 to control movement of the joints 116 and to control operations of the instruments 102 (e.g., through drive interfaces at the manipulators 114). In some embodiments, the control system 106 may also control some or all operations of the user input and feedback system 104, the auxiliary system 108, or other parts of the system 100. The control system 106 may include an electronic controller to control and/or assist a user in controlling operations of the manipulator assembly 110. The electronic controller comprises processing circuitry configured with logic for performing the various operations. The logic of the processing circuitry may comprise dedicated hardware to perform various operations, software (machine readable and/or processor executable instructions) to perform various operations, or any combination thereof. In examples in which the logic comprises software, the processing circuitry may include a processor to execute the software and a memory device that stores the software. The processor may comprise one or more processing devices capable of executing machine readable instructions, such as, for example, a processor, a processor core, a central processing unit (CPU), a controller, a microcontroller, a system-on-chip (SoC), a digital signal processor (DSP), a graphics processing unit (GPU), etc. In examples in which the processing circuitry includes dedicated hardware, in addition to or in lieu of the processor, the dedicated hardware may include any electronic device that is configured to perform specific operations, such as an Application Specific Integrated Circuit (ASIC), a Field Programmable Gate Array (FPGA), a Complex Programmable Logic Device (CPLD), discrete logic circuits, a hardware accelerator, a hardware encoder, etc. The processing circuitry may also include any combination of dedicated hardware and processor plus software.

As noted above, different manipulator systems 100 may have differing degrees of user control versus autonomous control, and embodiments disclosed herein may encompass fully user-controlled systems, fully autonomously-controlled systems, and systems having any mixture of user and autonomous control. For operations that are user-controlled, the control system 106 may generate the control signals in response to receiving a corresponding user input command input via the user input and feedback system 104. For example, if a user inputs a "roll instrument" input command, then the control system 106 may determine and send the appropriate control commands to the manipulator assembly 110 to cause the instrument 102 to roll. For operations that are autonomously controlled, the control system 106 may execute pre-programmed logic (e.g., a software program) and may determine and send control commands based on the programming (e.g., in response to a detected state or stimulus specified in the programming). In some systems, some operations may be user controlled and others autonomously controlled. Moreover, some operations may be partially user controlled and partially autonomously controlled—for example, a user input command may initiate performance of a sequence of events, and then the control system 106 may perform various operations associated with that sequence without needing further user input.

The auxiliary system 108 may comprise various auxiliary devices that may be used in operation of the manipulator system 100. For example, the auxiliary system 108 may include power supply units, auxiliary function units (e.g., functions such as irrigation, evacuation, energy supply, illumination that may support functionality of an instrument), sensors, display devices, etc. As one example, in a manipulator system 100 for use in a surgical context, the auxiliary system 108 may comprise a display device for use by medical staff assisting a procedure, while the user operating the input devices may utilize a separate display device that is part of the user input and feedback system 104. As another example, in a manipulator system 100 for use in a surgical context, the auxiliary system 108 may comprise flux supply units that provide surgical flux (e.g., electrical power) to instruments 102 (e.g., electrocautery surgical instruments). An auxiliary system 108 as used herein may thus encompass a variety of components and does not need to be provided as an integral unit.

Figure 2A:
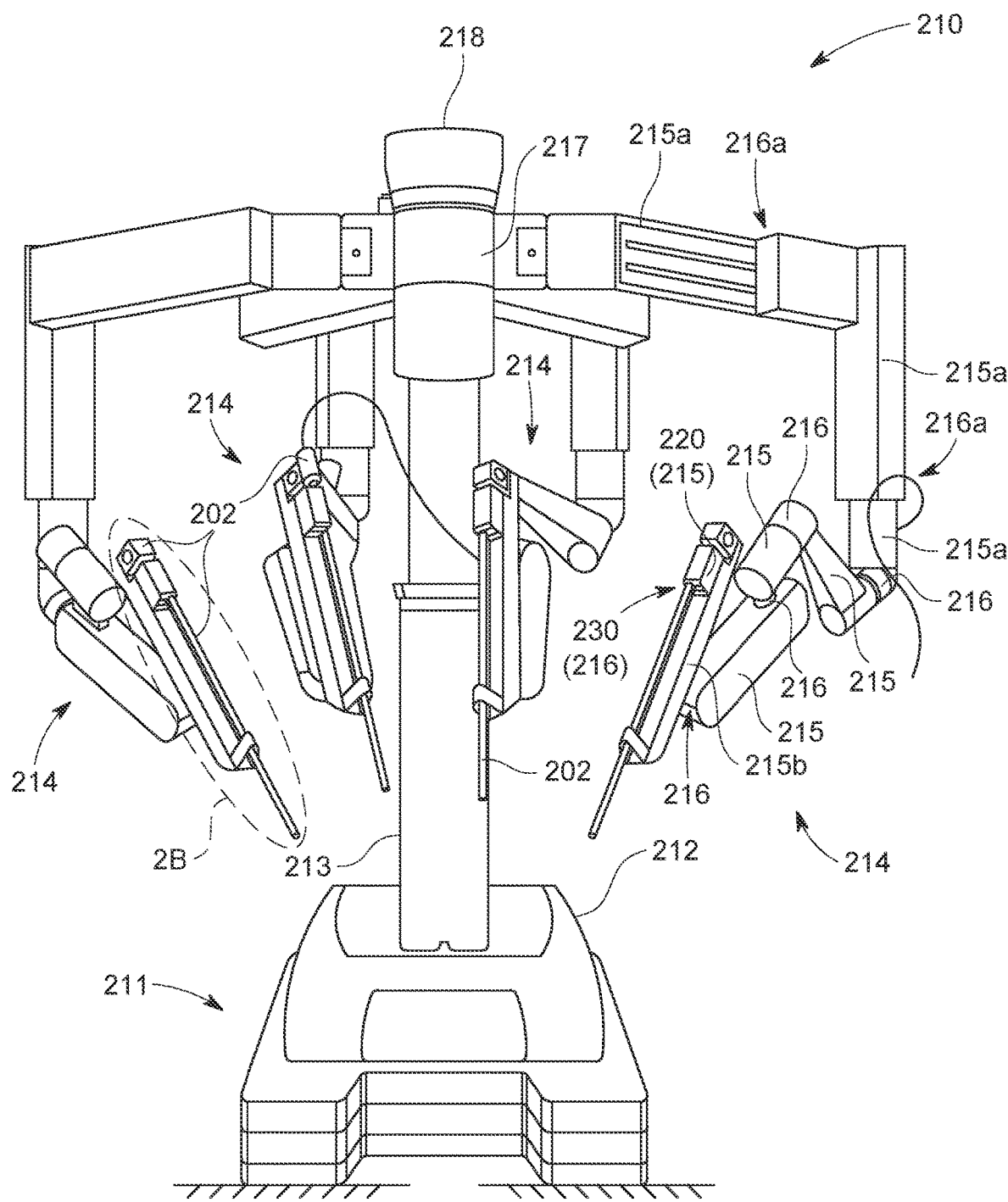
FIG. 2A is a perspective view of an embodiment of a medical manipulator system with instruments mounted to the manipulator arms.

FIG. 2A illustrates an embodiment of a manipulator assembly 210 of that can be used in a manipulator system, such as manipulator system 100. The manipulator assembly 210 is adapted for use in a medical context. In particular, the manipulator assembly 210 may be suitable for use in, for example, surgical, teleoperated surgical, diagnostic, therapeutic, and/or biopsy procedures. Such procedures could be performed, for example, on human patients, animal patients, human cadavers, animal cadavers, and portions or human or animal anatomy. The manipulator assembly 210 may also be used, for example, for non-surgical diagnosis, cosmetic procedures, imaging of human or animal anatomy, gathering data from human or animal anatomy, training medical or non-medical personnel, and procedures on tissue removed from human or animal anatomies (without return to the human or animal anatomy). Although this example is described in relation to the medical context, the principles, techniques, methods, and devices described herein may also be applied to non-medical manipulator systems 100, such as industrial manipulator systems, general robotic uses, and sensing or manipulating non-tissue work pieces. In non-limiting embodiments, the manipulator assembly 210 may be part of a teleoperated surgical system such as the da Vinci® Surgical Systems commercialized by Intuitive Surgical, Inc., of Sunnyvale, California. For example, embodiments disclosed herein may be (or be part of) a Model IS4000, marketed as the da Vinci® Xi™ Surgical System, commercialized by Intuitive Surgical, Inc. of Sunnyvale, California. Knowledgeable persons will understand, however, that inventive aspects disclosed herein may be embodied and implemented in various ways, including robotic and non-robotic embodiments and implementations. Implementations on da Vinci® Surgical Systems (e.g., the Model IS4000; the Model IS4200, marketed as the da Vinci® X™ Surgical System) are merely examples and are not to be considered as limiting the scope of the inventive aspects disclosed herein.

The manipulator assembly 210 comprises one or more manipulators 214. The manipulators 214 illustrated in FIG. 2A are one embodiment of the manipulators 114. FIG. 2A illustrates four manipulators 214, but the manipulator assembly 210 could include any number of manipulators 214, including one, two, three, or more. Each manipulator 214 is a kinematic structure comprising multiple links 215 and one or more joints 216, with each joint 216 movably coupling two adjacent links 215 together. Each joint 216 may impart one or more degrees of freedom to allow the links 215 coupled thereto to move relative to one another, such as allowing rotation, translation, or both. The links 215 and joints 216 of one of the manipulators 214 are labeled in FIG. 2A and described in greater detail below as an example.

In the example illustrated in FIG. 2A the manipulators 214 all have similar links 215 and joints 216. However, it should be understood that the manipulators 214 do not necessarily need to all have the same configurations—for example, one, some, or all of the manipulators 214 may have different numbers and/or types of links 215, joints 216, and instruments 202 as compared to others of the manipulators 214.

As noted above with respect to the joints 116, some of the joints 216 may be powered joints driven by a drive element. In some examples, a subset (one or more) of the joints 216 may be manually actuated. The links 215 coupled to a manually actuated joint 216 may be referred to, in some examples, as setup links. For example, in some embodiments, the setup links 215a in FIG. 2A are coupled to manually actuated joints 216a, and these setup links 215a may be manually moved into a desired configuration and locked into place during a setup phase before a procedure. Thereafter the remaining links 215 that are coupled to powered joints 216 may be moved under control of the control system 106 during the procedure. The shape, number, and arrangements of links 215 and joints 216 illustrated in FIG. 2A is merely one example, and in practice any number of links 215 (at least two) and any number of joints 216 (at least one) may be provided in the manipulator 214. Further, in some embodiments, the setup links 215a may be coupled to powered joints and may be moved via computer control.

The manipulators 214 may be coupled to a support structure 211, which supports the manipulators 214 relative to the ground/floor or relative to some other structure in the environment in which the manipulator assembly 210 is deployed. In the example illustrated in FIG. 2A, the support structure 211 comprises a base 212 that rests on the ground or floor, a vertical column 213 that extends vertically from the base 212, and an orienting platform 217 coupled to a top end portion of the vertical column 213. In some examples, the base 212 may include mobility components to facilitate movement of the base, such as wheels. In other examples the base 212 may lack such mobility components and may rest on the ground/floor or other structure. In some examples, the base 212 may be fixedly attached to the ground/floor or other structure, for example via mechanical fasteners, such as bolts, or via any other fastening mechanism. The vertical column 213 may be able to adjust in height, such as through a vertically telescoping mechanism. The manipulators 214 may be coupled to the orienting platform 217, and the orienting platform 217 may be configured to allow the manipulators to be rotated around the vertical column 213 (within some defined range of motion). The orienting platform 217 may also comprise a telescoping cantilever 218, which allows the orienting platform 217 to be moved horizontally from the vertical column 213. The support structure 211 illustrated in FIG. 2A is not limiting, and the manipulators 214 could be supported in other ways. For example, the manipulators 214 could be anchored to a wall, ceiling, table, cart, moveable base, non-movable base, or any other desired object. Moreover, the manipulators 214 could be coupled to separate support structures 211, rather than all being coupled to the same support structure 211. Moreover, the support structure 211 may have more or fewer degrees of freedom of movement than those shown in FIG. 2A, including no degrees of freedom. Moreover, in some examples the manipulator 214 may rest directly on, or be coupled directly to, the ground or floor or other structure, in which case the one of the links 215 of the manipulator 214 may serve as the support structure.

Figure 2B:
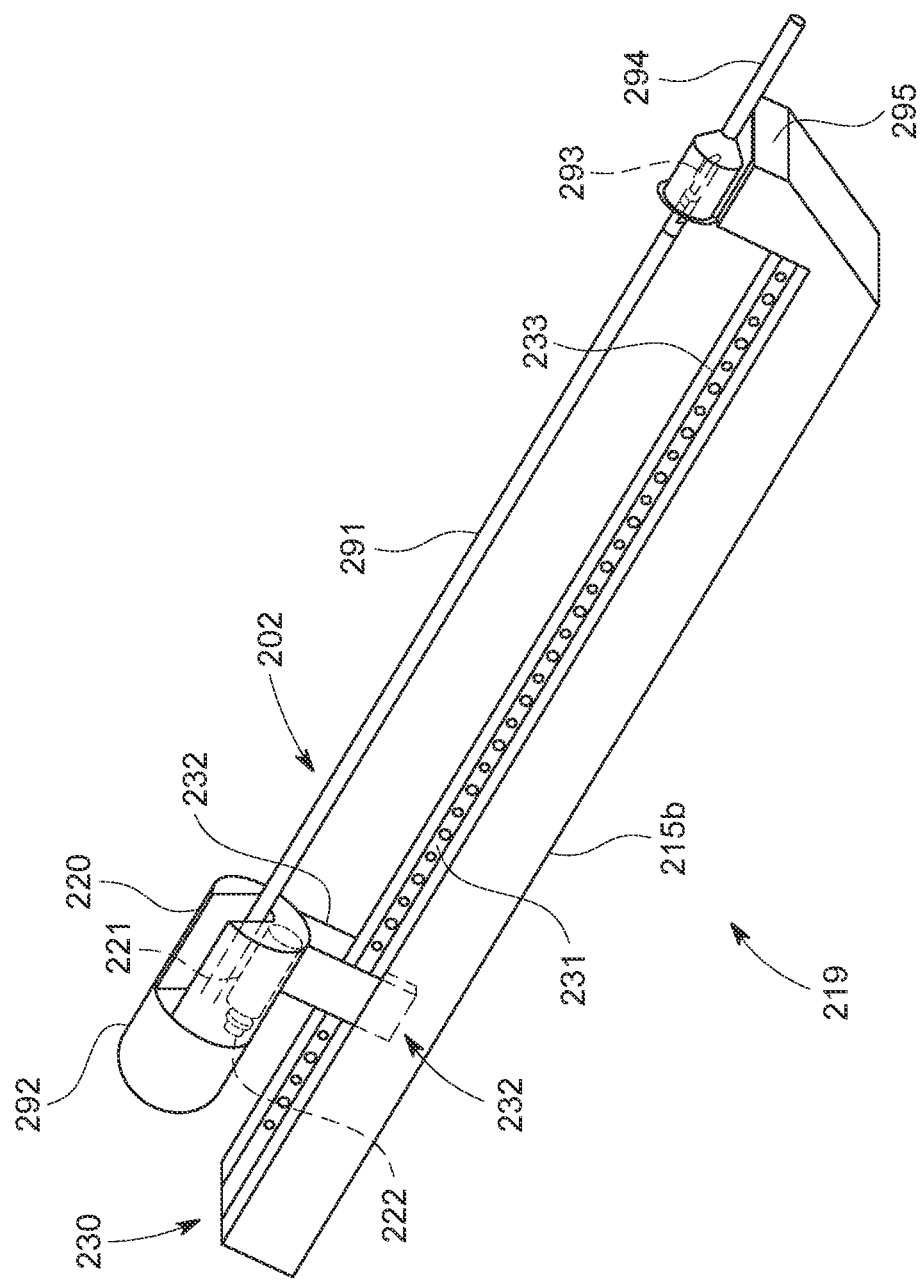
FIG. 2B is a detailed, perspective view showing interior components of detail 2B-2B of FIG. 2A, illustrating an instrument carriage coupled to a link of a manipulator arm and a medical instrument coupled to the instrument carriage.

As shown in FIGS. 2A and 2B, one or more of the links 215 may be configured as an instrument holder 219 to support and drive an instrument 202 coupled thereto. The instrument holder 219 includes a link 215b that may serve as an instrument holder frame, another link that will be referred to as an instrument carriage 220, and an accessory mount portion 295 to mount an accessory such as a cannula 294. The instrument carriage 220 physically supports the mounted instrument 202 and has one or more actuators 221 to provide driving forces to the instrument 202 to control operations of the instrument 202. The actuators 221 may provide the driving forces by actuating drive outputs 222, such as rotary disc outputs, joggle outputs, linear motion outputs, etc. The drive outputs 222 may interface with and mechanically transfer driving forces to corresponding drive inputs of the instrument 202 (directly, or via intermediate drive outputs, which may be part of a sterile instrument adaptor (ISA) of a sterile drape assembly). The ISA may be placed between the instrument 202 and the instrument carriage 220 to maintain sterile separation between the instrument 202 and the manipulator. The instrument carriage 220 may also comprise other interfaces (not illustrated), such as electrical interfaces to provide and/or receive electrical signals to/from the instrument 202.

As shown in FIGS. 2A and 2B, the instrument carriage 220 is coupled to the link 215b by one of the joints 216, which will be referred to hereinafter as the prismatic joint 230. Specifically, the prismatic joint 230 causes the instrument carriage 220 to translate relative to the link 215b along a longitudinal dimension of the link 215b (direction T in FIG. 2B). Thus, when the prismatic joint 230 is operated, the prismatic joint 230 causes the instrument 202, which is coupled to the instrument carriage 220, to translate relative to the link 215b along an axis. The axis along which the instrument 202 translates may correspond to a central axis of the instrument shaft 291 of the instrument 202, which is described in greater detail below. In some examples, the instrument 202 may be translated along this axis in order to insert the instrument 202 into (or remove the instrument 202 from) the workspace (e.g., the patient), and therefore this axis may be referred to as the "insertion axis."

The prismatic joint 230 comprises a carriage base 232, a track 231, and a cable drive system (not visible in FIGS. 2A and 2B) that comprises one of the capstan mechanisms disclosed herein. The instrument carriage 220 is coupled to the carriage base 232, the carriage base 232 is slidably coupled to the track 231, and the track 231 is coupled to the link 215b. The carriage base 232 is driven to translate along the track 231 by the cable drive system, an embodiment of which is described in greater detail below with reference to FIG. 3. The translation of the carriage base 232 along the track 231 results in the instrument carriage 220 translating relative to the link 215b as described above.

As shown in FIG. 2B, the instrument 202 comprises an instrument shaft 291 (also referred to herein as shaft 291) and an end effector 293 attached to the shaft 291 at a distal end portion of the instrument 202. The end effector 293 may be configured to perform one or more operations, such as grasping, cutting, delivering flux, stapling, etc. The end effector 293 may also be moveable relative to the shaft 291, for example via a wrist mechanism. The instrument 202 may also comprise an instrument transmission housing 292, which in some embodiments, may be located at a proximal end portion of the instrument 202. The instrument transmission housing 292 is attached to the shaft 291 and is configured to couple the instrument 202 to the instrument carriage 220. The instrument transmission housing 292 may comprise drive inputs that interface with and are driven by the drive outputs 222 of the instrument carriage 220 (directly or via an intermediary such as an ISA), and a force transfer mechanism to convert the motion of the drive inputs into motion that drives degrees of freedom of the instrument 202. For example, the forces and motion imparted from the instrument carriage 220 may be converted by the force transfer mechanism of the instrument transmission housing 292 into movement of cables or rods that extend through the shaft 291, with the motion of the cables or rods controlling movement and/or actuation of the shaft 291, a wrist mechanism, and/or the end effector 293. In some embodiments as described in more detail below with reference to FIGS. 12A and 12B, the force transfer mechanism in the instrument transmission housing 292 may comprise a cable drive system that utilize one or more of the capstan mechanisms disclosed herein. In such an embodiment, a capstan of the capstan mechanism may be driven to rotate by forces transferred from the drive outputs 222 of the instrument carriage 220 with rotation of the capstan driving movement of cables that extend through the shaft 291 to drive actuation or movement of a portion of the instrument (e.g., to articulate a wrist of the instrument and/or the end effector 293).

The link 215b may comprise an accessory mount portion 295, for example near a distal end portion of the link 215b. The accessory mount portion 295 may be configured to mount an accessory, such as a surgical cannula 294, as illustrated in FIG. 2B. The surgical cannula 294 may be inserted into an opening in the patient, and the end effector 293 and shaft 291 of the instrument 202 may be inserted into the patient through the cannula 294. The prismatic joint 230 may control the insertion and removal of the instrument 202 through the cannula 294 by translating the instrument carriage 220 along the track 231. In some examples, a remote center of motion of the manipulator assembly 210 (described in greater detail below) may be located so as to coincide with a portion of the cannula 294.

The manipulator assembly 210 is adapted for use in a medical context, and thus the instruments 202 may include medical instruments. Medical instruments may comprise surgical instruments (e.g., grasping instruments, cutting instruments, electrocautery instruments, stapling instruments, suturing instruments, etc.), imaging instruments (e.g., endoscopes), diagnostic instruments, and therapeutic instruments, which can have a variety of configurations, for example, with and without end effectors. In the example illustrated in FIGS. 2A and 2B, each manipulator 214 has one instrument 202, but in other examples multiple instruments 202 may be coupled to the same manipulator 214. In some examples in which multiple instruments 202 are coupled to the same manipulator 214, the manipulator 214 may have multiple prismatic joints 230 (e.g., one for each instrument 202). In other examples in which multiple instruments 202 are coupled to the same manipulator 214, the manipulator may have a prismatic joint 230 that drives multiple instruments 202.

In some examples, the manipulator assembly 210 may be configured such that as the instruments 202 are moved by the manipulators 214, the motion of a respective instrument 202 is constrained such that the instrument shaft 291 always passes through a fixed point (or region) of space, which may be referred to as a remote center of motion. In other words, the manipulator 214 moves as if the instrument 202 were constrained by a pivot point on the instrument shaft 291 (i.e., the remote center of motion), with the instrument 202 being able to rotate about the pivot point or translate along a line passing through the pivot point, but not being able to move away from the pivot point. For example, during a surgical procedure, this remote center of motion may be made to correspond to an opening in a patient through which the instruments are inserted into the patient, so that as the instruments are moved during the procedure the instruments pivot through the opening but do not move laterally relative to the opening. This may enable the opening to be smaller than would otherwise be needed, and may reduce damage to surrounding tissue that results from movement of the instruments. Such constraint on the motion of the manipulators 214 around a remote center of motion may be imposed mechanically by the structure of the manipulators 214 themselves, or they may be imposed by logic programmed into the control system 106. In some embodiments, the remote center of motion coincides with a position along a portion of the cannula 294.

Figure 3:
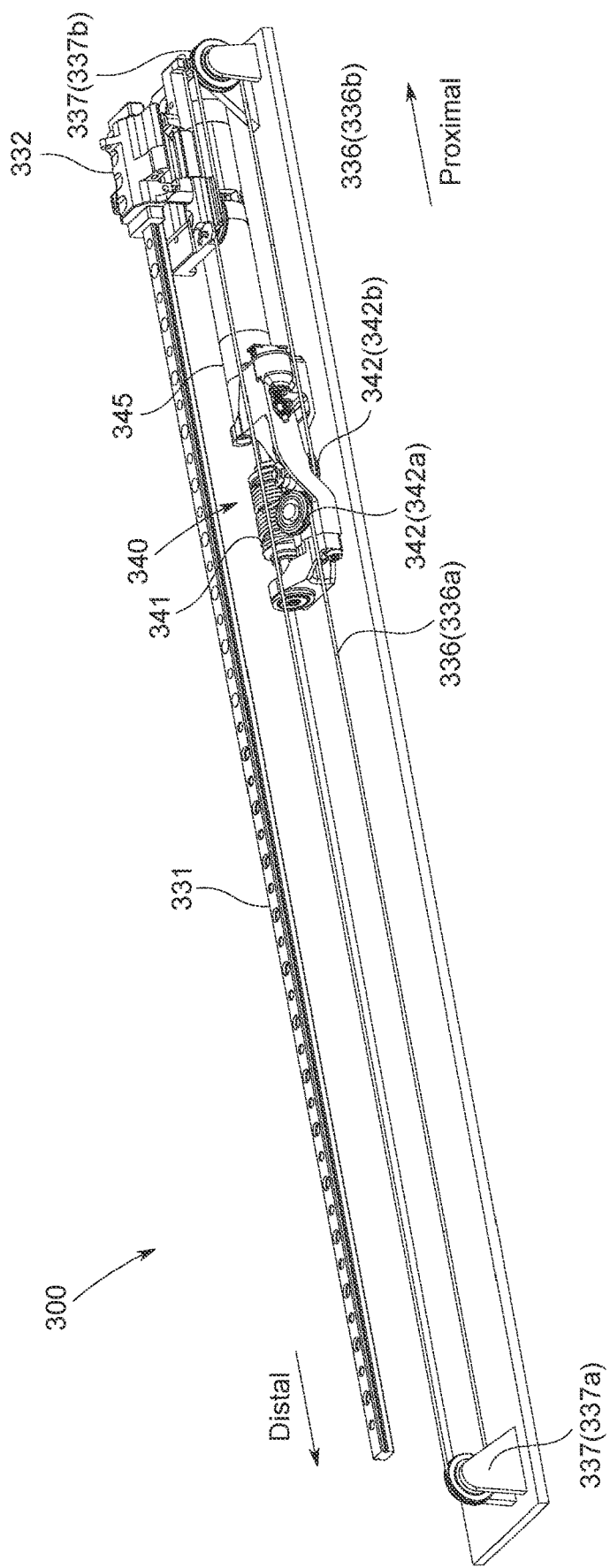
FIG. 3 is a perspective view of an embodiment of a cable-driven prismatic joint.

FIG. 3 illustrates a cable driven prismatic joint 330 (also referred to as joint 330 or prismatic joint 330) according to an example embodiment. The joint 330 may be used to couple together two links of a manipulator such that the two links can translate relative to one another. For example, the joint 330 may be used as a prismatic joint 230 of a manipulator 214 of the manipulator assembly 210. In some embodiments, the joint 330 may be used to couple the link 215b with the instrument carriage 220. The joint 330 comprises a track 331, a carriage base 332 slidably coupled to a track 331, cables 336 (e.g., cables 336a, 336b), coupled to the carriage base 332 to move the carriage base 332 along the track 331, pulleys 337 (e.g., pulleys 337a, 337b), to redirect the cables 336, and a traveling capstan mechanism 340 to drive the cables 336. The track 331 may be coupled to one link of the manipulator, such as the link 215b, and the carriage base 332 may be coupled to another link of the manipulator, such as the instrument carriage 220. Thus, as the carriage base 332 moves along the track 331, the motion causes relative translation between the two links (e.g., movement of the carriage base 332 causes the instrument carriage 220 to translate relative to the link 215b).

As noted above, the carriage base 332 is coupled to one or more cables 336 that move the carriage base 332 along the track 331. Any number and arrangement of cables 336 may be used. In the embodiment of FIG. 3, a first cable 336a is coupled to the carriage base 332 to move the carriage base 332 along the track 331 in one direction (e.g., a distal direction), and a second cable 336b is coupled to the carriage base 332 to move the carriage base 332 along the track 331 in an opposite direction (e.g., a proximal direction). In other embodiments, the cables 336a and 336b may be two portions of the same cable 336, rather than two separate cables 336. For example, cable 336a may be a first cable portion and cable 336b may be a second cable portion, each cable portion being part of the same cable 336. The cable(s) 336 may be routed through the joint 330 via pulleys 337. For example, as shown in FIG. 3, a first pulley 337a may be disposed near a distal end portion of the joint 330 and a second pulley 337b may be disposed near a proximal end portion of the joint 330 (with distal and proximal directions in the orientation of FIG. 3 being labeled), with the carriage base 332 located between the two pulleys 337a, 337b. The first and second pulleys 337a, 337b redirect the first and second cables 336a, 336b so that the cables 336a, 336b run along a path that is roughly aligned with a length of the track 331. With this arrangement, retracting the first cable 336a while extending the second cable 336b causes the carriage base 332 to move distally along the track 331 toward the first pulley 337a, and retracting the second cable 336b while extending the first cable 336a causes the carriage base 332 to move proximally along the track 331 towards the second pulley 337b.

As noted above, the joint 330 comprises a traveling capstan mechanism 340 (also referred to as capstan mechanism 340) to control the retraction and extension of the cable(s) 336. Embodiments of capstan mechanisms that can be used as the capstan mechanism 340 are shown in greater detail in FIGS. 4A-5C and described below. Referring further to FIG. 3, the traveling capstan mechanism 340 comprises a capstan 341, take-up pulleys 342 (e.g., take-up pulleys 342a, 342b), and a drive element 345. The capstan 341 is a device onto which the cables 336 may be wound by rotating the capstan 341. The capstan 341 provides for length conservation of the cables 336 when the carriage base 332 is moved by having the cables 336 wind onto and off of the capstan 341. The capstan 341 may have a number of cable rotations positioned around the capstan 341 to account for pay-in and pay-out of the cables and the changing effective length of the cables 336a, 336b as the carriage base 332 moves. In some embodiments, multiple capstans 341 are provided, for example a separate one for each of the cables 336. The capstan 341 may be generally cylindrical in shape, and may have grooves in a radially outward facing surface thereof to guide the cables 336 to wind onto the capstan 341 in a controlled manner as the capstan rotates. The take-up pulleys 342 redirect the cable(s) 336 to wind onto or unwind off from the capstan 341. The capstan 341 may be coupled to a drive shaft, and the drive shaft in turn may be coupled to the drive element 345 such that the drive element 345 can drive rotation of the capstan 341. The drive element 345 may be any device that can impart torque to a shaft to drive rotation of the capstan 341. For example, the drive element 345 may be an electric motor, a pneumatic or hydraulic rotary actuator, or a mechanical force transfer mechanism (e.g., rotary disc) that receives forces from some other drive element through mechanical coupling and transfers and/or converts the forces into rotation for the capstan 341, etc. The drive element 345 may be controlled by a control system 106 of a manipulator system 100 in which the joint 330 is included.

Rotating the capstan 341 in one direction tends to wind the first cable 336a onto the capstan 341 (retracting the first cable 336a) and unwind the second cable 336b off from the capstan 341 (extending the second cable 336b), and conversely rotating the capstan 341 in an opposite direction tends to unwind the first cable 336a off from the capstan 341 (extending the first cable 336a) and wind the second cable 336b onto the capstan 341 (retracting the second cable 336b). Accordingly, the translation of the carriage base 332 along the track 331 can be controlled by controlling the direction and amount that the capstan 341 rotates.

The traveling capstan mechanism 340 is configured to provide relative translation between the capstan 341 and the take-up pulleys 342 as the capstan 341 rotates (i.e., the capstan 341 and the take-up pulleys 342 can translate relative to one another as the capstan 341 rotates), such that the take-up angles of the cables 336 remain constant. Relative translation of the capstan 341 and the take-up pulleys 342 can include translation of the capstan 341 relative to some reference point (e.g., such as a link of a manipulator to which the capstan is coupled) while the take-up pulleys 342 remain translationally fixed relative to the reference point, or translation of the take-up pulleys 342 relative to the reference point while the capstan 341 remains translationally fixed relative to the reference point. In embodiments in which the capstan 341 translates relative to the reference point while the take-up pulleys 342 do not, a drive shaft (e.g., a spline shaft) may be used to enable the translation of the capstan 341 along the drive shaft while the capstan 341 also rotates with the drive shaft about an axis of the drive shaft. In embodiments in which the take-up pulleys 342 translate relative to the reference point while the capstan 341 does not, a support structure to which the take-up pulleys 342 are attached may be movably coupled to a track or other mechanism to enable translation of the take-up pulleys 342 relative to the capstan 341.

The traveling capstan mechanism 340 also comprises a guide element (not visible in FIG. 3) that is translationally fixed relative to the take-up pulleys 342 and engages a cable spooling groove of the capstan 341 to force relative translation between the capstan 341 and the take-up pulleys 342 as the capstan 341 rotates. For example, the capstan 341 may translate axially along the drive shaft as the capstan 341 rotates. The relative translation between the capstan 341 and the take-up pulleys 342 as the capstan 341 rotates eliminates take-up angle deviation, as described above. The guide element may be any element that can engage the groove of the capstan 341 to cause translation of the capstan 341 and take-up pulleys 342 relative to one another. In the embodiments illustrated in FIGS. 4-6 (described further below), the guide element rotates and rolls along the outer surface of the capstan 341 in the groove, and thus the guide element is referred to below as a guide roller. In other embodiments, the guide element does not rotate. These and other aspects of the traveling capstan mechanism 340 will be described in greater detail below with reference to FIGS. 4-6.

FIGS. 4A-D illustrate an embodiment of a traveling capstan mechanism 440 (also referred to as capstan mechanism 440 or mechanism 440) in accordance with the present disclosure. The traveling capstan mechanism 440 can be used in a cable drive system of a joint, instrument, or other cable driven device, to drive movement of cables. For example, the traveling capstan mechanism 440 can be used in the cable drive system of the joint 230 and/or in a cable drive system of an instrument 202, as described above with reference to FIG. 2B. The traveling capstan mechanism 440 may be used as an embodiment of the traveling capstan mechanism 340. As shown in FIGS. 4A-D, the traveling capstan mechanism 440 comprises a capstan 441, take-up pulleys 442 (e.g., take-up pulleys 442a, 442b), a drive element 445, a guide roller 446, and a support structure 447. As described in more detail below, the capstan 441 is mounted onto a drive shaft 443, and rotation of the drive shaft 443 is driven by the drive element 445. The support structure 447 may support various parts of the traveling capstan mechanism 440, and may be coupled to a link of the manipulator system, such as the link 215b in FIG. 2B. The take-up pulleys 442 and the drive shaft 443 of the capstan mechanism 440 may be coupled to the support structure 447 by bearings 465 such that take-up pulleys 442 and the shaft 443 can rotate, but are held translationally stationary relative to the support structure 447. The capstan 441, on the other hand, may translate relative to the support structure 447 along the drive shaft 443, as described in greater detail below.

The cables 436 are wound onto a radially outward-facing surface of the capstan 441. This surface has a cable spooling groove 444 (groove 444) formed therein, which extends helically around and along the capstan 441. The groove 444 guides the cables 436 to spool onto the capstan 441 in an orderly manner as the capstan 441 rotates. The groove 444 comprises raised regions (e.g., ridges) and lowered regions (e.g., troughs). The raised regions of the groove 444 may be similar to, and may be referred to as, threads, and the groove 444 may be similar to and may be referred to as a threaded portion. However, unlike some threads, the groove 444 is configured to spool cables 436 rather than to fasten.

Figure 4A:
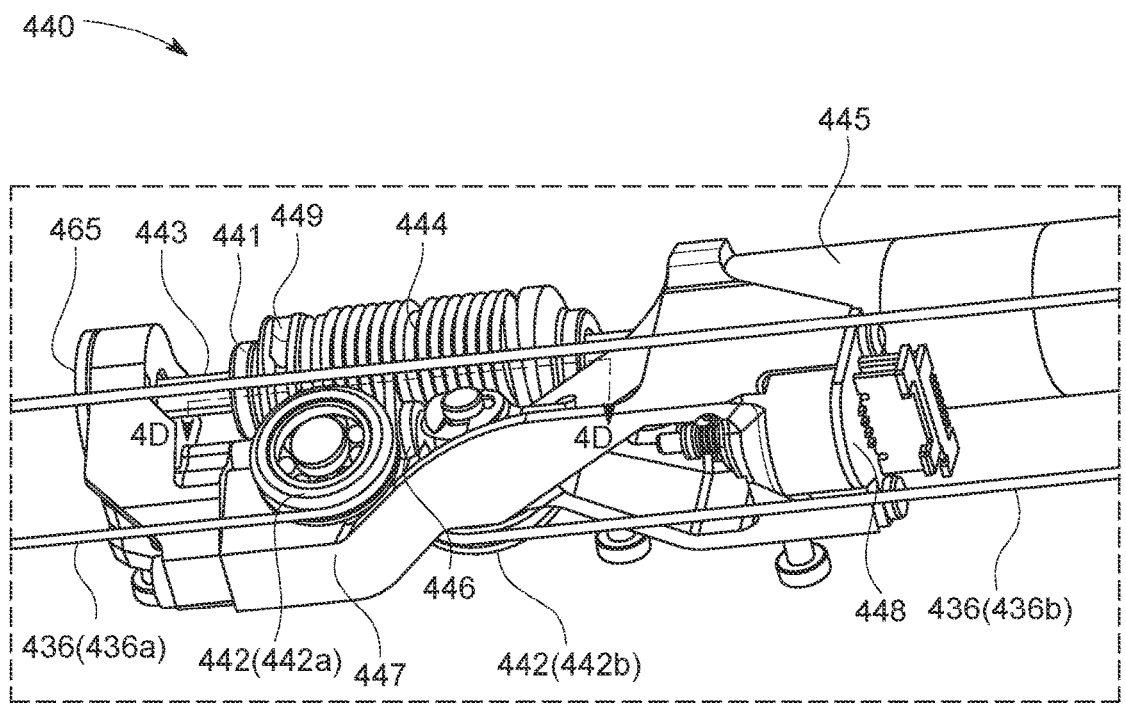
FIG. 4A is a detailed perspective view of an embodiment of a traveling capstan mechanism disclosed herein.
Figure 4B:
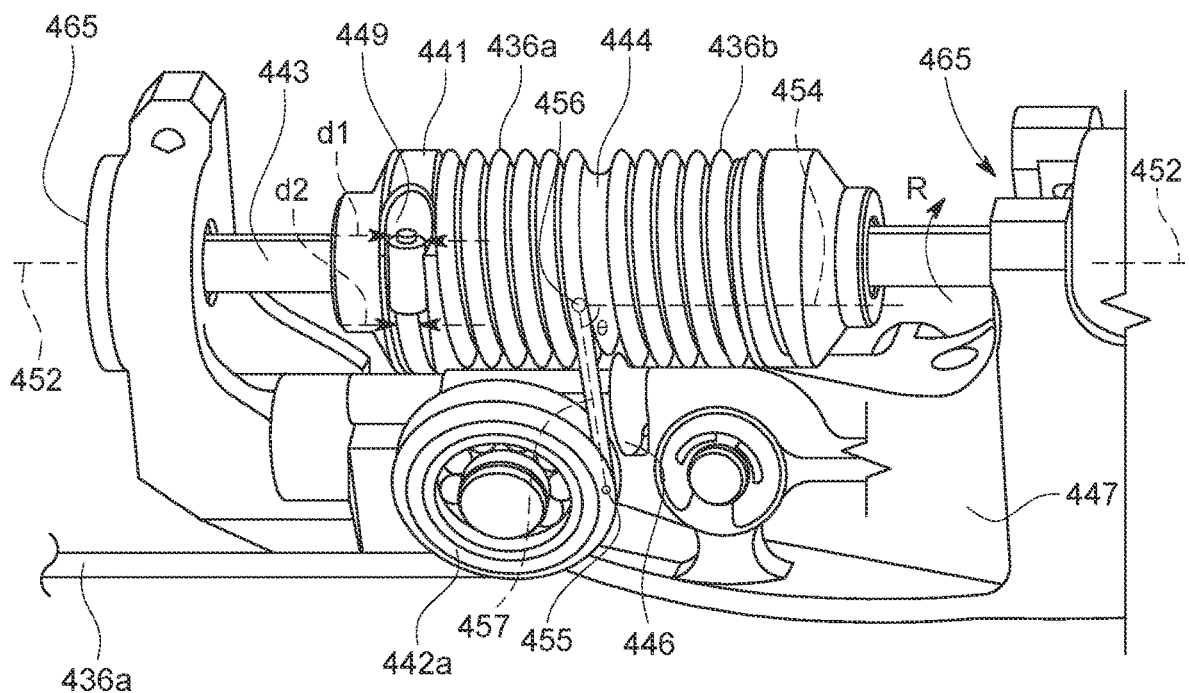
FIG. 4B. is another detailed perspective view of the embodiment of the traveling capstan mechanism of FIG. 4A.
Figure 4C:
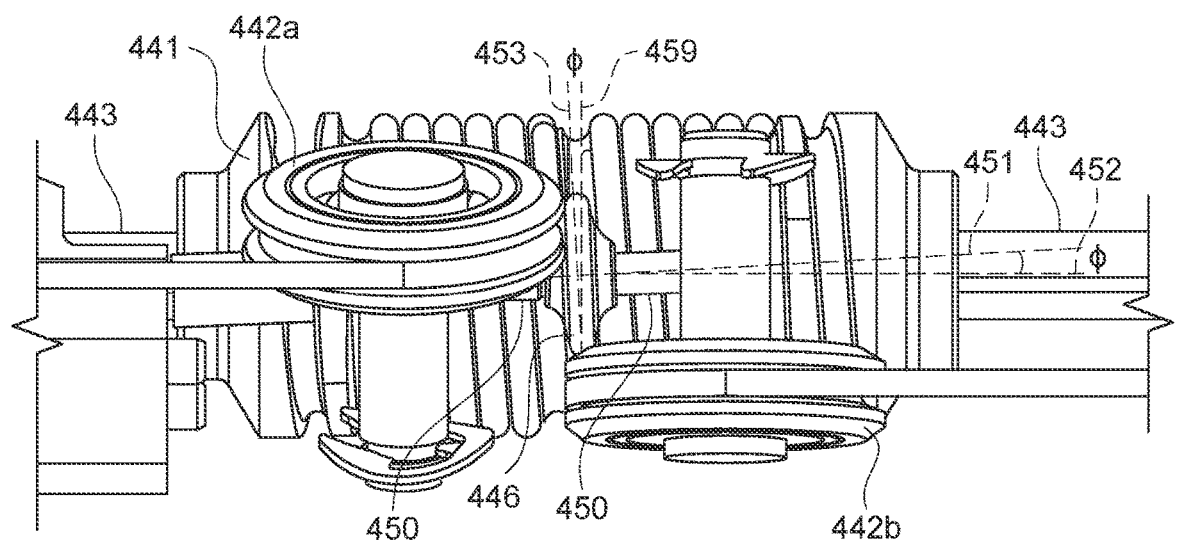
FIG. 4C. is yet another detailed perspective view of the embodiment of the traveling capstan mechanism of FIG. 4A.
Figure 4D:
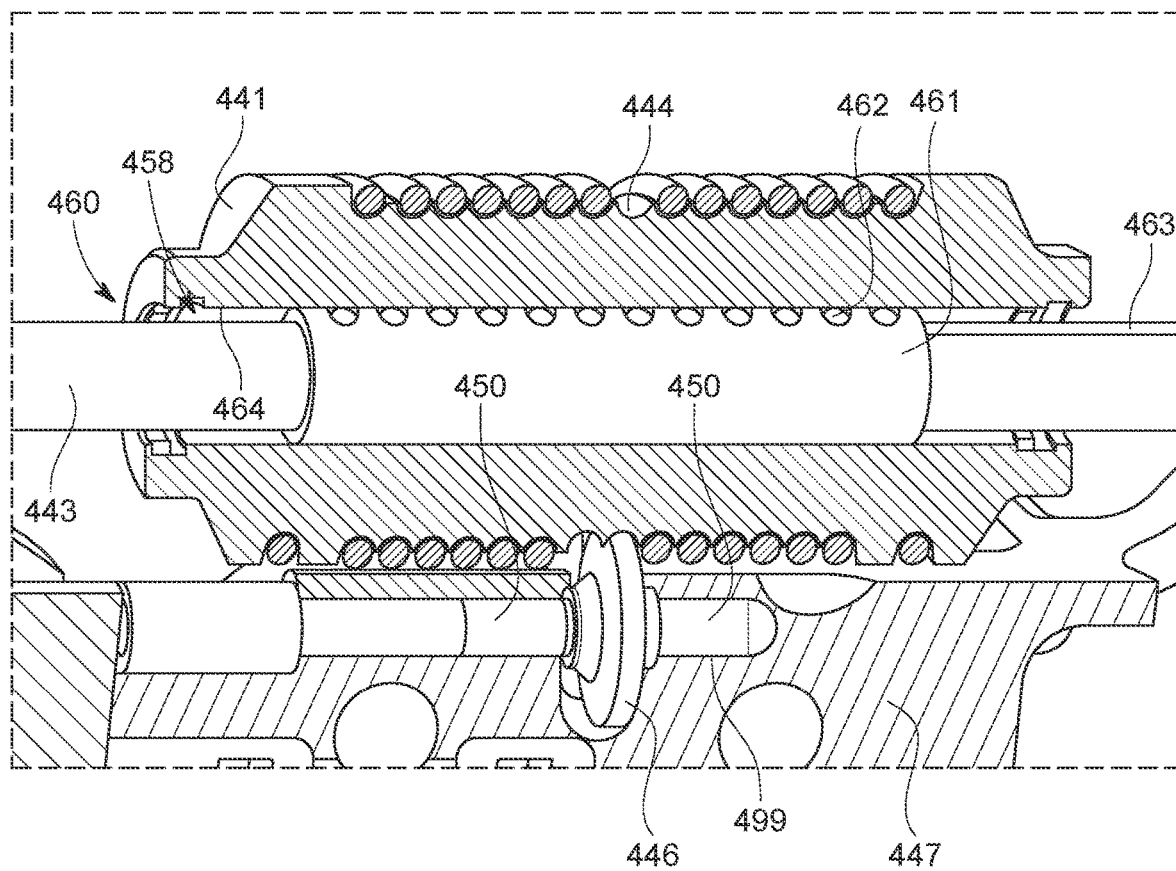
FIG. 4D. is a cutaway perspective view of the embodiment of the traveling capstan mechanism of FIG. 4A, with the cutaway taken through the cross-section 4D-4D.

In the example illustrated in FIGS. 4A-D, two cables 436a, 436b are wound onto the capstan 441. However, any number of cables 436 could be used. For example, the cables 436a, 436b could be two parts of the same cable 436 rather than two separate cables 436. For example, cable 436a may be a first cable portion and cable 436b may be a second cable portion, each cable portion being part of the same cable 436. A first take-up pulley 442a guides the first cable 436a onto the capstan 441, and a second take-up pulley 441b guides the second cable 436b onto the capstan 441. The two cables 436 may be wound onto the same groove 444 of the capstan 441, although each cable 436 may occupy different portions of the groove 444 at any given time. In the state illustrated in FIGS. 4A-4D, the first cable 436a is occupying windings of the groove 444 on a left half of the capstan 441, while the second cable 436b is occupying windings of the same groove 444 on a right half of the capstan 441. The term "winding" in this context refers to a segment of the groove 444 corresponding to one revolution around the capstan 441. As more of the first cable 436a is wound onto the capstan 441, the second cable 463b simultaneously unwinds from the capstan 441 and the take-up locations of the cables 436 will move rightward along the capstan 441. Conversely, as the first cable 436a is unwound from the capstan 441, the second cable 463b simultaneously winds more onto the capstan 441 and the take-up locations of the cables 436 will move leftward along the capstan 441. This winding and unwinding of the cables 436 provides for length conversation of the cables 436 as described above. The take-up location 456 of the first cable 436a is illustrated in FIG. 4B, and is discussed in greater detail below. Left and right directions are being used herein with reference to the orientation of FIGS. 4A-4D As shown in FIG. 4D, the capstan 441 also comprises a bore 458 through a longitudinal central axis of the capstan 441. The longitudinal central axis of the capstan 441 is aligned with an axis of rotation 452, which is shown in FIG. 4A and described in greater detail below. The drive shaft 443 may be a spline shaft that passes through the bore 458 and is coupled to capstan 441 via the bore 458. The drive shaft 443 is part of a ball spline mechanism 460 (also referred to as spline mechanism 460) that causes the drive shaft 443 to drive rotation of the capstan 441 (i.e., the capstan 441 rotates along with rotation of the drive shaft 443), while the drive shaft 443 permits the capstan 441 to translate along an axial length of the drive shaft 443 (i.e., the drive shaft 443 does not restrict translation of the capstan 441 relative to the axial length of the drive shaft 443). In one example illustrated in FIG. 4D, the ball spline mechanism 460 comprises a tube 461 circumferentially surrounding the drive shaft 443 and arranged between the drive shaft 443 and an inner surface (radially inward facing surface) of the bore 458 of the capstan 441. The spline tube 461 has openings holding balls 462, wherein the balls 462 are in contact with the drive shaft 443 on one side of the balls 462 and in contact with the capstan 441 on the other side of the balls 462. The balls 462 provide a rolling bearing for the capstan 441 relative to the shaft 443, allowing the capstan 441 to translate axially along the shaft 443 with little friction. The balls 462 are also disposed partially within a groove 463 in the drive shaft 443 and partially in a groove 464 in a surface of the bore 458 opposite from the groove 463 (the surface of the bore 458 comprising the groove 464 may also be referred to herein as a radially inward facing surface). The grooves 463 and 464 constrain the balls 462 so that the balls 462 can only move along an axial direction of the drive shaft 443 and bore 458. This constraint locks the capstan 441 and shaft 443 relative to one another in terms of rotation. Thus, the spline mechanism 460 causes the drive shaft 443 to drive rotation of the capstan 441, while also allowing the capstan 441 to freely translate along the length of the drive shaft 443. The spline mechanism 460 illustrated in FIG. 4D is just one non-limiting embodiment, and any other type of mechanism may be used, such as a toothed spline, involute spline, keyway shaft, polygonal shaft (e.g., square, hexagon), lobed etc. For example, another embodiment of a spline mechanism is illustrated in FIG. 5C and discussed below, and this could be used in the capstan mechanism 440 in lieu of the spline mechanism 460.

As shown in FIGS. 4A-D, the traveling capstan mechanism 440 also comprises a guide element 446. As noted above, in this embodiment the guide element 446 is configured to rotate and roll along the capstan 441, and thus the guide element 446 is also referred to herein as a guide roller 446. As shown in FIG. 4D, the guide roller 446 is coupled to the support structure 447 by shaft 450. The shaft 450 is passes through a central bore (not visible in the figure) in the guide roller 446 and is housed within a slot 499 in the support structure 447. The shaft 450 constrains translation of the guide roller 446 relative to the support structure 447 while allowing the guide roller 446 to rotate about an axis of rotation 451, as shown in FIGS. 4C and 4D. Bearing surfaces are present between the internal diameter the guide roller 446 (in the central bore) and the external diameter of shaft 450, and between faces of the support structure 447 in the slot 499 and the end faces of the roller 446. As shown, these are all sliding contact/plain bearings, which may be lubricated with grease or oil to reduce friction. Material combinations or surface treatments may also be chosen to reduce friction, wear, or galling. Alternatively, the shaft 450 may be integral with the roller, and the shaft may rotate inside the support structure 447. In either scenario, the sliding/plain bearing interfaces may be replaced with other types of bearings, such as any of: deep-groove ball bearings, angular contact bearings, cylindrical roller bearings, thrust bearings, tapered roller bearings, etc.

The guide roller 446 is in contact with the capstan 441 in the groove 444 of the capstan 441. Therefore, as the capstan 441 rotates, the guide roller 446 can roll along the outer radial surface of the capstan 441 following the path defined by the groove 444. Because the groove 444 spirals helically around and along the capstan 441 and the guide roller 446 follows the groove 444 as the capstan 441 rotates, rotation of the capstan 441 forces the capstan 441 and the guide roller 446 to be translated axially relative to one another. The guide roller 446 is held stationary relative to the support structure 447, and therefore the axial translation of the capstan 441 and the guide roller 446 relative to one another results in axial translation of the capstan 441 relative to the support structure 447. In other words, as the capstan 441 rotates, the guide roller 446 forces the capstan 441 to translate along the drive shaft 443.

As described above, translation of the capstan 441 along the drive shaft 443 as the capstan 441 rotates may prevent take-up angle deviation between the capstan 441 and the take-up locations of the cables 436. In particular, as capstan 441 rotates in one direction, the first cable 436a winds onto the capstan at the take-up location 456 and the axial position of the take-up location 456 relative to the axial length of the capstan 441 shifts at a rate of one winding of the groove 444 per rotation of the capstan 441. However, as the capstan 441 rotates, the guide roller 446 causes the capstan 441 to translate axially relative to the take-up pulley 442a in an opposite direction by a distance equal to the width of one winding of the groove 444 per rotation of the capstan 441. Therefore, the translation of the capstan 441 in one direction cancels out the translation of the take-up location 456 along the length of the capstan 441 in the opposite direction, resulting in the take-up location 456 remaining stationary relative to the take-up pulley 442a as the capstan 441 rotates. Because the take-up location 456 remains stationary relative to the take-up pulley 442a, the take-up angle θ between the cable 436a and the capstan 441 (see FIG. 4B) remains constant as the capstan 441 rotates. The same is true for rotation of the capstan 441 in the opposite direction. Although the description above focuses on the cable 436a and the take-up pulley 442, the same description is also applicable to the other cables 436 (e.g., 436b) and their associated take-up pulleys 442 (e.g., 442b).

In one embodiment, optionally, it may be desirable for the take-up angle θ to be controlled such that the cable 436a is aligned with the groove 444 as the cable 436a winds and unwinds from the capstan 441. This may reduce friction and wear of the cable 436a as the cable 436a winds onto the capstan 441 and reduce the likelihood of the cable 436a jumping out of the groove 444. In other words, if the helix angle of the groove 444 is φ, then the take-up angle θ may be set equal to 90°-φ. The take-up angle θ may be defined as the angle between the take-up axis 457 of the cable 436 and a line 454 that is parallel to the rotational axis 452 of the capstan at the take-up location 456. As shown in FIG. 4B, the take-up axis 457 is the direction the cable 436 runs as the cable 436 extends between the pulley take-up location 455 and the capstan take-up location 456, where the pulley take-up location 455 is the location where the cable 436 joins the take-up pulley 442 and the capstan take-up location 456 is the location along the capstan 441 at which the cable 436a joins the capstan 441. The helix angle of the groove 444 corresponds to the angle between the slope of groove 444 and the normal plane 459 of the capstan 441. The helix angle may also be referred to as the "lead angle." The normal plane 459 of the capstan 441 is a plane perpendicular to the capstan rotation axis 452.

In an embodiment, the guide roller 446 may be tilted relative to the rotation axis 452 of the capstan 441, so that a normal plane 453 of the guide roller 446 is more closely aligned with the slope of the groove 444. In particular, as illustrated in FIG. 4C, the rotational axis 451 of the guide roller 446 (guide roller axis 451) may be tilted by a non-zero angle φ relative to the rotational axis 452 of the capstan 441 (capstan axis 452) (i.e., the guide roller axis 451 is nonparallel to the capstan axis 452), which causes the normal plane 453 of the roller 446 to be tilted by the angle φ relative to a normal plane 459 of the capstan 441. The normal plane 453 of the roller 446 is a plane perpendicular to the rotation axis 451 of the roller 446. By tilting the normal plane 453 relative to the normal plane 459, the guide roller 446 may be better aligned with slope of the groove 444, which may allow the guide roller 446 to roll more smoothly within the groove 444 with less friction generated and a lower likelihood of the guide roller 446 skipping out of the groove 444. More specifically, in some embodiments, the angle φ may desirably be equal to the aforementioned helix angle (aka lead angle) of the groove 444 relative to the normal plane 459, which results in precise alignment of the guide roller with the groove 444. The helix (lead) angle is determined by the diameter of the cable, the width of the groove, and the number of helix starts. In the embodiment of FIGS. 4A-4D, each winding of the groove 444 is spaced relatively closely together to minimize the overall axial length of the capstan, but in other embodiments the windings could be spaced further apart, which results in a larger helix (lead) angle. Having further spaced apart windings may allow the groove walls to be taller because there is more material left between each groove, but also results in the capstan 431 having a longer axial length.

The drive shaft 443 may be coupled to the drive element 445. The drive element 445 may impart force or torque to the drive shaft 443 to drive rotation of the drive shaft 443, and thereby drive rotation of the capstan 441. The drive element 445 is an example of the drive element 345 already described above, and thus duplicative description of the drive element 445 will be omitted.

Optionally, the traveling capstan mechanism 440 may also include a position sensor 448 (see FIG. 4A). The position sensor 448 may sense the rotations of the capstan 441, and feed this information (e.g., a sensed amount of rotation) back to a controller, such as the control system 106 of FIG. 1. The controller may use this information to monitor the state of the traveling capstan mechanism 440, including monitoring how many revolutions the capstan 441 has been rotated and in which directions. For example, the position sensor 448 may include a rotary encoder that is coupled to the drive shaft 443 and/or some portion of the drive element 445, for example via gears, such that each rotation of the shaft 443 causes the rotary encoder to rotate by a predetermined amount. As another example, the position sensor 448 could be a translational sensor that measures the axial position of the capstan 441. Since the rotation of the capstan 441 is coupled to its translation, the amount of rotation of the capstan 441 can be inferred from the translation of the capstan 441.

The capstan 441 may also comprise a groove terminal 449 at each end of the groove 444, which may allow end portions of the cables 436 to be secured to the capstan 441 to ensure there is no slippage of the cables 436 relative to the capstan 441 as the capstan 441 rotates. For example, the groove terminals 449 may comprise a generally tubular structure coupled to an end portion of the groove 444, with the tubular structure having a larger diameter or width $d_1$ in a first region and a smaller diameter or width $d_2$ in a second region. The groove terminal 449 may be configured such that a cable stop affixed to the end of the cable 436 may fit within the groove terminal 449 in the first region, but cannot be drawn through the second region with the smaller diameter. Thus, the cable 436 is secured to the capstan 441. The tubular structure of the groove terminal 449 may be partially enclosed circumferentially with an opening through which the cable 436 may be passed to make insertion of the cable 436 into the groove terminal 449 easier. This is one embodiment of the groove terminal 449, and other types of groove terminal 449 could be used instead. For example, the cables 436 could be secured to the capstan 441 via a fastener (e.g., screw, clamp, peg, etc.), by welding, by tying, crimping, etc.

Figure 5A:
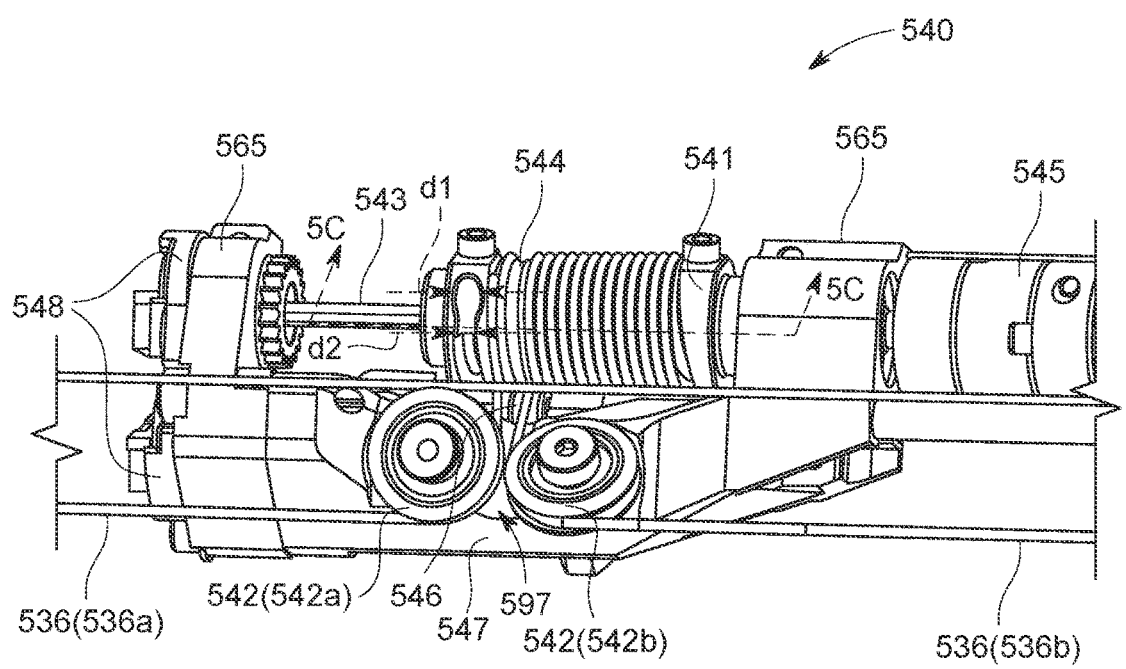
FIG. 5A is a perspective view of another embodiment of a traveling capstan mechanism.
Figure 5B:
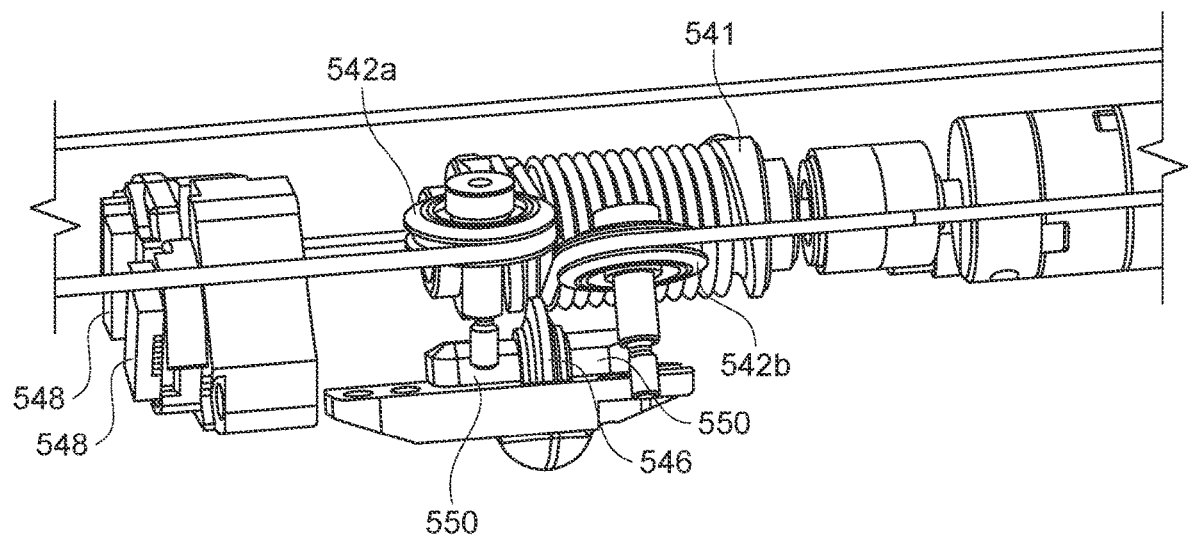
FIG. 5B. is another perspective view of the embodiment of the traveling capstan mechanism of FIG. 5A.
Figure 5C:
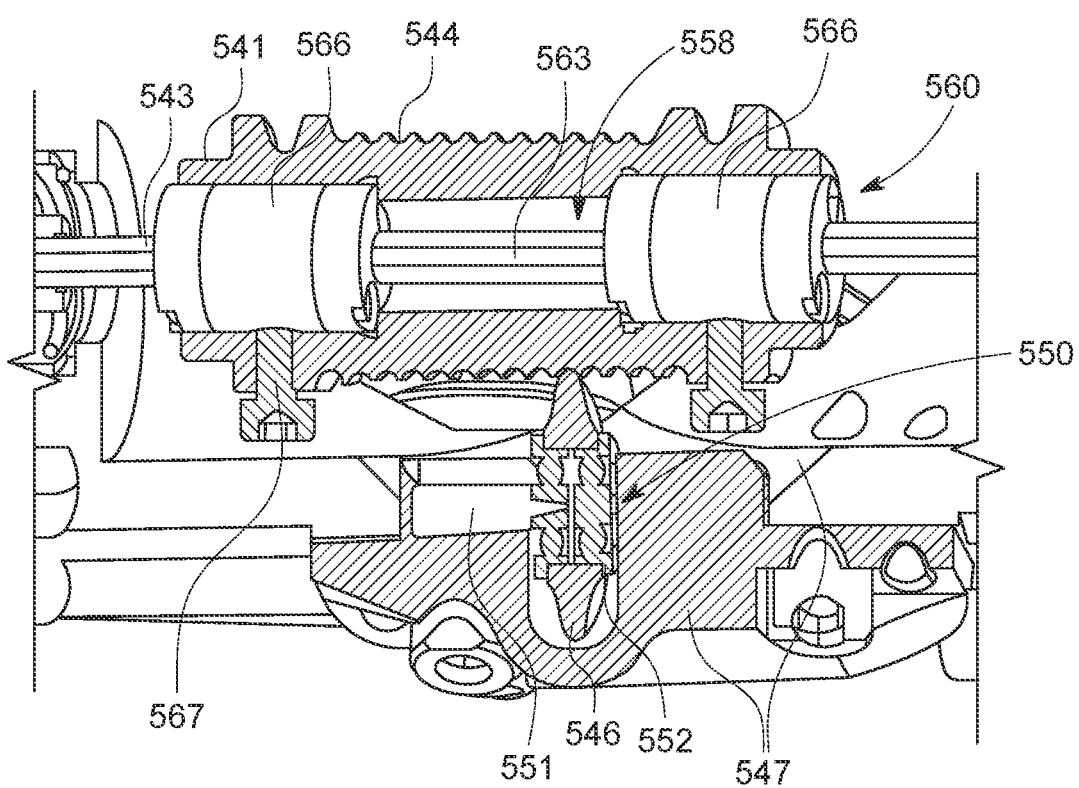
FIG. 5C. is a cutaway perspective view of the embodiment of the traveling capstan mechanism of FIG. 5A, with the cutaway taken through the cross-section 5C-5C.

FIGS. 5A-C illustrate another embodiment of a traveling capstan mechanism 540 (capstan mechanism 540 or mechanism 540). The traveling capstan mechanism 540 can be used in a cable drive system of a joint, instrument, or other cable driven device, to drive movement of cables. For example, the traveling capstan mechanism 540 can be used in the cable drive system of the joint 230 and/or in a cable drive system of an instrument 202, as described above with reference to FIG. 2B. The traveling capstan mechanism 540 can be used as the traveling capstan mechanism 340. The traveling capstan mechanism 540 has various parts that are similar to corresponding parts of the traveling capstan mechanism 440 already described above. The descriptions above of the parts of the mechanism 440 apply equally to the corresponding parts of the mechanism 540, unless indicated otherwise or logically contradictory, and thus detailed descriptions of these parts and may be omitted to avoid duplicative description.

As illustrated in FIGS. 5A-C, like the traveling capstan mechanism 440, the traveling capstan mechanism 540 comprises a capstan 541, take-up pulleys 542 (e.g., take-up pulleys 542a, 542b), a drive shaft 543, a guide element 546, a support structure 547, optional position sensors 548, and a drive element 545. Furthermore, like the capstan 441, the capstan 541 has a cable spooling groove 544 formed in a radially-outward facing surface thereof, and may include groove terminals 549. In this embodiment, the guide element 546 can rotate and roll along the capstan 541, and thus is also referred to herein as a guide roller 546.

The traveling capstan mechanism 540 differs from the traveling capstan mechanism 440 in three main ways: first, the guide roller 546 and take-up pulleys 542 are positioned differently in the capstan mechanism 540 than the guide roller 446 and take-up pulleys 442 in the capstan mechanism 440; second, a different ball spline mechanism 560 is used to couple the capstan 541 to the drive shaft 543; and third, the position sensors 548 are located in a different position than the position sensors 448.

As can be seen partially in FIG. 5A and more clearly in FIG. 5B (the support structure 547 has been omitted in FIG. 5B to improve visibility), in the mechanism 540, both of the take-up pulleys 542a, 542b are positioned on the same side of the support structure 547, i.e., on or above a top face 597 of the support structure 547, and the guide roller 546 is positioned on the opposite side of the support structure, i.e., on or below a bottom face of the support structure, with the guide roller 546 being located at a circumferential position around the longitudinal axis of the capstan 541 that is offset from the circumferential position of the take-up pulleys 542. In contrast, in the mechanism 440, the take-up pulleys 442a, 442b are positioned on opposite sides of the support structure 447 and the guide roller 446 is positioned between the two take-up pulleys 442 at approximately the same circumferential position as the take-up pulleys 442 (see, e.g., FIG. 4C). The arrangement of the guide roller 546 and take-up pulleys 542 illustrated in FIGS. 5A-C may be beneficial in some circumstances in that this arrangement may afford more room for the guide roller 546, and thus a larger diameter guide roller 546 may be used and/or larger diameter bearings 550 may be used. For example, as illustrated in FIG. 5C, the bearings 550 may be ball bearings, comprising a bearing shaft 551 fixedly coupled to the support structure 547, a bearing hub (flange) 552 coupled to the guide roller 546, and balls (not illustrated) between the bearing shaft 551 and bearing hub 552 to allow rotation of the bearing hub 552 relative to the bearing shaft 551. A larger guide roller 546 and/or larger bearings 550 may allow for a reduction in the rolling friction. On the other hand, the arrangement of the guide roller 446 illustrated in FIGS. 4A-C may allow for a more compact design. In other embodiments, the guide element (e.g., guide roller 446 or 546) is positioned differently. In particular, the guide element (e.g., guide roller 446 or 546) can be located anywhere around the circumference of the capstan.

As can be seen in FIG. 5C, the ball spline mechanism 560 used in the traveling capstan mechanism 540 comprises two ball spline units 566 coupled to the drive shaft 543. The ball spline units 566 may be self-contained ball-spline units that are physically coupled to capstan 541, for example via fasteners 567. In FIG. 5C, the fasteners 567 are set screws, but in other embodiments the fasteners 567 could be any type of mechanical fastener, such as bolts, rivets, etc. In some embodiments, the fasteners 567 are omitted and the capstan 541 is attached to the ball spline units 566 by other fastening means, such as adhesives, a keyway, press-fitting, welding, etc. In one embodiment, the ball spline units 566 are recirculating ball splines (also referred to herein as recirculating ball spline units). Use of the ball spline mechanism 560, with recirculating ball splines, may afford the capstan 541 a larger translational range of motion. On the other hand, the ball spline mechanism 560 may require a larger bore 558 diameter than in the ball spline mechanism 460, and this together with the height of the fasteners 567 may result in the overall size (e.g., radial width) of the capstan 541 being larger than that of the capstan 441.

As can be seen in FIGS. 5A and 5B, the position sensors 548 are positioned at the end of the shaft 543 opposite from the drive element 545, as opposed to near the drive element 545 as in the mechanism 440. One position sensor 548 may be coupled directly to the shaft 543, while another position sensor 548 may be coupled to the shaft 543 or to the other sensor 548 via gears. Multiple sensors 548 are included in some embodiments to facilitate the determining of the absolute position within multiple turns. For example, the sensors 548 may comprise rotary encoders that may be geared such that the encoder of one sensor 548 does not rotate as fast the other, and by calculating the offset between the encoders of the sensors 548 one can determine the absolute position within multiple turns. Those having ordinary skill in the art would appreciate that any number of position sensors can be used with various placements as desired to attain precise control over the capstan and/or for redundancy.

The principles of operation of the traveling capstan mechanism 540 are the same as those of the traveling capstan mechanism 440 already described above, and thus duplicative description thereof is omitted.

The traveling capstan mechanisms 440 and 540 are described herein as illustrative embodiments of the traveling capstan mechanism 340, but should not be considered as limiting. Other traveling capstan mechanisms contemplated herein include mixtures of the various parts and features described in relation to the mechanism 440 and the mechanism 540. In particular, the positioning of the guide roller 446/546 and pulleys 442/542, the type of ball spline mechanism 460/560 that is used, and the positioning and number of position sensors 448/548 may be chosen as desired by one of ordinary skill in the art based on a variety of factors, such as overall space requirements, friction considerations, costs etc. In addition, various other types of guide elements can be used in embodiments of traveling capstan mechanisms similar to the mechanisms 440 and/or 540 in lieu of the guide rollers 446/546. For example, the guide rollers 446 or 546 may be replaced with guide elements that do not rotate or roll along the capstan 441/541, such a non-rotating disc, a wedge, an arm, a convex helical segment with similar helix angle as the groove 441/541 and configured to engage with (e.g., fit at least partially within) the groove 441/541, or any other rigid member that can engage with the groove 441/541.

In addition, in some example embodiments, the capstan may be translationally stationary relative to some reference point (such as the drive element that drives the capstan, a link of a manipulator to which the capstan is coupled, the ground supporting the manipulating system, etc.), and the relative motion of the capstan and the take-up pulleys may be provided by the take-up pulleys translating relative to the reference point. In this case, the guide element and the take-up pulleys may be mounted to a moveable substructure that is translatable in the axial direction relative to the capstan. For example, the substructure may be mounted to a rail or other mechanism that allows the substructure to move in a direction substantially parallel to the axis of rotation of the capstan. The substructure may replace the support structure 447/547 described above, and the guide element and the take-up pulleys may be coupled to the substructure in the same or similar manner as the take-up pulleys 442/452 are coupled to the support structure 447/547. In these embodiments, the guide element is engaged with the capstan groove in the same manner as described above with respect to the mechanisms 440/450, and thus when the capstan rotates, the interaction between the guide element and the groove forces relative translation between the take-up pulleys and the capstan in the same manner as described above, except that in this case, the substructure and thus the take-up pulleys attached to the substructure translate relative to the reference point. In this example, because the capstan does not translate, the shaft that drives motion of the capstan does not necessarily need to be a spline shaft, and the spline elements may also be omitted. In these embodiments, other aspects of the capstan mechanism may be similar to those of the capstan mechanisms 440/540 described above, and thus duplicative description of these details is omitted.

As noted above, embodiments described herein can mitigate the take-up angle deviation while also allowing for a relatively compact capstan mechanism and relatively low friction. An explanation of how embodiments bring about these benefits will now be provided in greater detail.

As noted above, in some embodiments, the dimensions in a radial direction of the drive system (e.g., traveling capstan mechanism, pulleys, etc.) are the same as, or only slightly larger than, the dimensions in the radial direction of a similar drive system lacking the constraint mechanism (e.g., guide roller) for causing the capstan to travel. This may be enabled, for example, due to the constraint mechanism (e.g., guide roller) being relatively small and/or being located in a space that would otherwise be unoccupied in the drive system without such a constraint mechanism. For example, in the embodiment of FIGS. 4A-4D, the guide roller 446 is positioned radially adjacent the capstan between the take-up pulleys 442a, 442b in a region of space that might otherwise be unoccupied, and thus the addition of the guide roller 446 does not increase the dimensions of the drive system in the radial direction. Moreover, even in embodiments in which the constraint mechanism does increase the size of the drive system in the radial direction, the increase may be small, especially when compared to the size increase of other approaches designed to address take-up angle deviation. Specifically, in the alternative approach described above that relies on moving a take-up pulley radially away from the capstan, the envelope of the drive system may need to be increased significantly in a radial direction in order to allow the take-up pulley to be sufficiently far from the capstan to sufficiently reduce the take-up angle deviation.

Figure 9D:
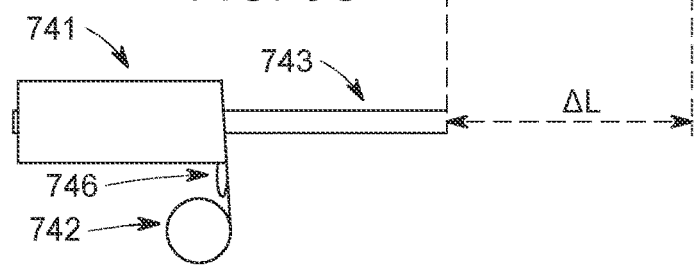
Figure 9E:
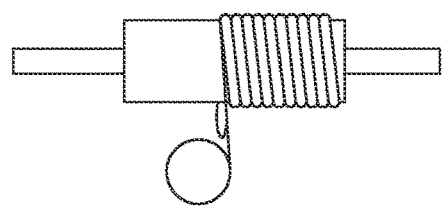
Figure 9F:
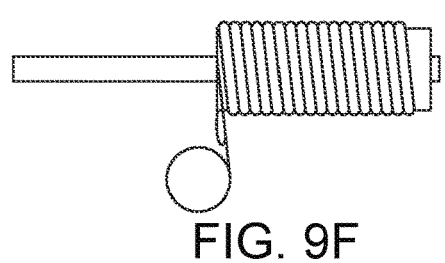

In addition, in some embodiments, the dimensions of the drive system for the traveling capstan mechanisms described herein in an axial direction are also smaller than in other alternative approaches. For example, FIGS. 9A-9F illustrate the difference in axial length between a traveling capstan 791 of the alternative approach described above which utilizes threading to cause translation of the capstan 791 and an embodiment of a traveling capstan 741 disclosed herein. The traveling capstan 791 of the alternative approach has a threaded hub 792 engaged with a threaded passageway 793, and travels along the shaft 794. A take-up pulley 742 directs a cable onto the capstan 741. FIGS. 9A-C illustrate the capstan 791 of the second approach traveling through its full range of motion. The traveling capstan 741 according to embodiments disclosed herein comprises a guide element 746 engaged with the groove of the capstan and travels along the shaft 743. FIGS. 9D-9F illustrate the capstan 741 disclosed herein traveling through its full range of motion. As can be seen by comparing FIGS. 9C and 9D, the length of the hub 792 in the second approach may result in the total axial length required for the assembly being longer than the axial length required for the capstan 741 disclosed herein. In some cases, the difference in length ΔL may be nearly as long as the capstan itself. Accordingly, in some circumstances, embodiments disclosed herein may be more compact in a radial dimension, an axial dimension, or both, as compared to other solutions for addressing take-up angle deviation.

Furthermore, as noted above, the friction generated in embodiments disclosed herein may be less than in alternative approaches. One source of friction resulting from the constraint mechanism causing relative motion of the capstan and the take-up pulleys is sliding friction due to lateral surfaces of the guide element sliding relative to the lateral surfaces of the groove as the capstan rotates. However, the region of sliding contact between the lateral surfaces of the guide element and the lateral surfaces of the groove at any given time has a relatively small surface area, and therefore the sliding friction resulting from this contact is relatively small. This sliding friction may be further minimized by selecting a relatively lubricious material for the guide element, such as PTFE, UHMW, Acetal, brass or bronze, Nitronic 60, or other similar materials. Moreover, in examples in which the guide element is a rolling component, such as guide roller 446 or 546, the rolling action of the guide element along the groove may even further reduce the sliding friction generated. The rotation of the rolling component may generate some rotational friction of the bearings that support the rolling component, but such rotational friction of the bearing may be small, especially if a low friction bearing such as a ball bearing or roller bearing is used. Thus, the total friction generated by the interaction of the constraint mechanism with the capstan is relatively small. In contrast, in the second approach described above, the threaded hub and the threaded passageway slide relative to one another as the shaft rotates with a relatively larger area of sliding contact, and with no rolling action, and thus more friction is generated.

Figure 6:
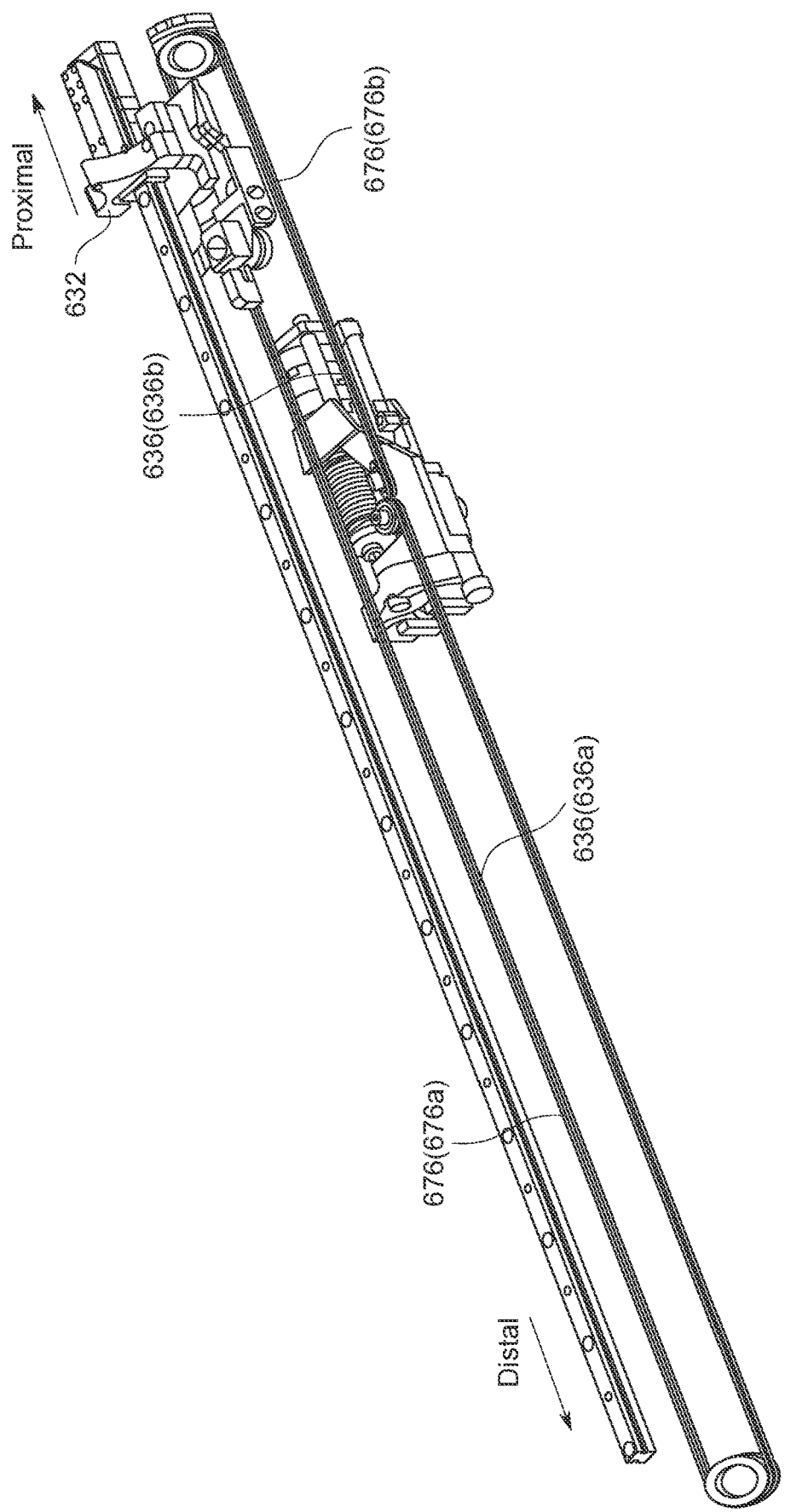
FIG. 6 is a perspective view of another embodiment of a cable-driven prismatic joint.

FIG. 6 illustrates another embodiment of a prismatic joint that utilizes backup cables. As described above, the backup cables can be incorporated to allow the overall prismatic joint to maintain operation in the event that the corresponding primary cable is damaged, permitting uninterrupted, normal operation of the manipulator system. Further, use of the backup cables may increase safety of the device and prevent the mechanism driven by the cables from inadvertent and undesired movement in the event of primary cable failure. Moreover, use of backup cables can increase the time between maintenance of the system. In addition, when two or more cables are used, their diameters may be made smaller than if just one cable were used, as the combined strength of the smaller diameter cables may equal that of the larger diameter cable. Furthermore, using smaller diameter cables can reduce the bending stress experienced by the cables as they are wrapped around pulleys and the capstan.

The prismatic joint 630 is an embodiment of the prismatic joint 330 and includes primary cables 636 (e.g., cables 636a, 636b) and backup cables 676 (e.g., cables 676a, 676b). As illustrated, a first backup cable 676a is routed alongside a first primary cable 636a, and both are coupled to a first side of the carriage base 632 to move the carriage base 632 in a distal direction. A second backup cable 676b is routed alongside a second primary cable 636b, and both may be coupled to a second side of the carriage base 632 to move the carriage base 632 in a proximal direction.

Figure 7:
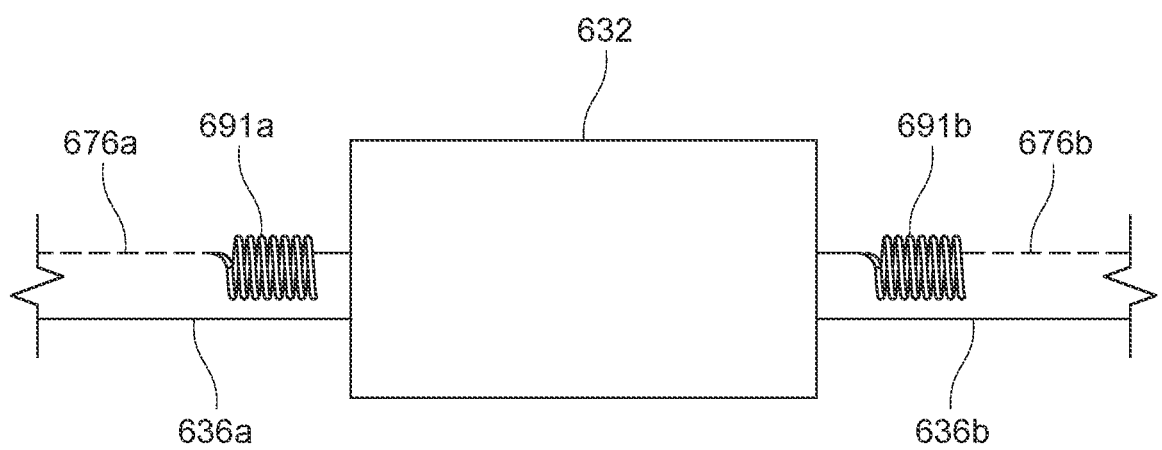
FIG. 7 is a schematic illustration of cables and springs coupled to a carriage base of the embodiment of the cable-driven prismatic joint of FIG. 6.

As described above, the backup cables 676 may be configured to experience less stress than the primary cables 636 while being used concurrently. In one embodiment, as illustrated in the schematic view of FIG. 7, this is accomplished by coupling springs 691 in series with the backup cables 676. For example, springs 691a and 691b may be coupled in series with backup cables 676a and 676b, respectively. The springs 691 may have a stiffness ranging from 50% to 1000% of the stiffness of the primary cables 636. In some embodiments, the stiffness of the springs 691 may range from 50% to 400% of the stiffness of the primary cables 636. The specific locations and configurations of the springs 691 may be different than what is illustrated in FIG. 6B. For example, the springs 691 may be offset to account for stretch under working loads when the backup cable 676 starts taking over the full working load when the primary cable 636 effectively fails. Coupling a spring 691 in series with the backup cable 676 reduces the stress the backup cable 676 experiences because the series coupling reduces the amount that the backup cable 676 is stretched (e.g., the amount of change in length) under load as compared to the primary cable 636. In particular, because the backup cable 676 and spring 691 are in series, they both will undergo stretching when a tensile load is applied and the total distance stretched for the combined assembly of backup-cable-plus-spring 691 is the sum of their individual stretching. In other words: $d_{total}=d_{backup}+d_{spring}$, where d denotes the distance stretched. Furthermore, because the primary cable 636 and the backup-cable-and-spring-assembly are arranged in parallel to share the load, they must stretch by the same amount. In other words, $d_{primary}=d_{total}=d_{backup}+d_{spring}$. From this it can be seen that the distance the backup cable 676 is stretched ($d_{backup}$) must be less than the distance the primary cable 636 is stretched ($d_{primary}$), with the difference being equal to the distance the spring 691 is stretched ($d_{spring}$). The stress experienced by each cable under a load is related to the distance the respective cable is stretched (along with other properties of the cables), and therefore, all other things being equal, the backup cable 676 experiences less stress than the primary cable 636 because it is stretched a smaller distance.

In another embodiment, the backup cables 676 can have material properties that enable them to experience less stress than the primary cables 636. For example, the backup cables 676 can be made of a material that has a lower elastic modulus than that of the primary cables 636. Example material pairings would be a primary cable made from a steel alloy, stainless steel alloy, or cobalt chrome alloy (all roughly 190-230 GPa elastic moduli) paired with a backup cable made from Titanium or a Titanium alloy (roughly 90-120 GPa elastic moduli). Similarly, a primary cable made from a Tungsten alloy or doped Tungsten (roughly 400 GPa elastic moduli) could be paired with a backup cable made from a steel alloy, stainless steel alloy, or cobalt chrome alloy to achieve the same effect. Reducing the elastic modulus of the backup cable 676 as compared to the primary cable 636 reduces the stress of the backup cable 676 as compared to the primary cable 636. In particular, the stress experienced by each cable is related not only to the distance it is stretched, but also the elastic modulus of the cable (among other properties). Thus, all other things being equal, the cable with the lower elastic modulus will experience less stress.

Although the backup cables 676 are described above in relation to a prismatic joint and capstan mechanism, it should be understood that the backup cables 676 could be used with any cable driven joint that uses a capstan mechanism, such as a rotational joint. In addition, although the cables 636a, 636b, 676a, and 676b are illustrated as all wrapping on to the same capstan, in some embodiments multiple capstans may be provided for groups of cables and/or for individual cables. For example, the cables 636a and 676a could be routed to a first capstan and the cables 636b and 676b could be routed to a second capstan.

Figure 8A:
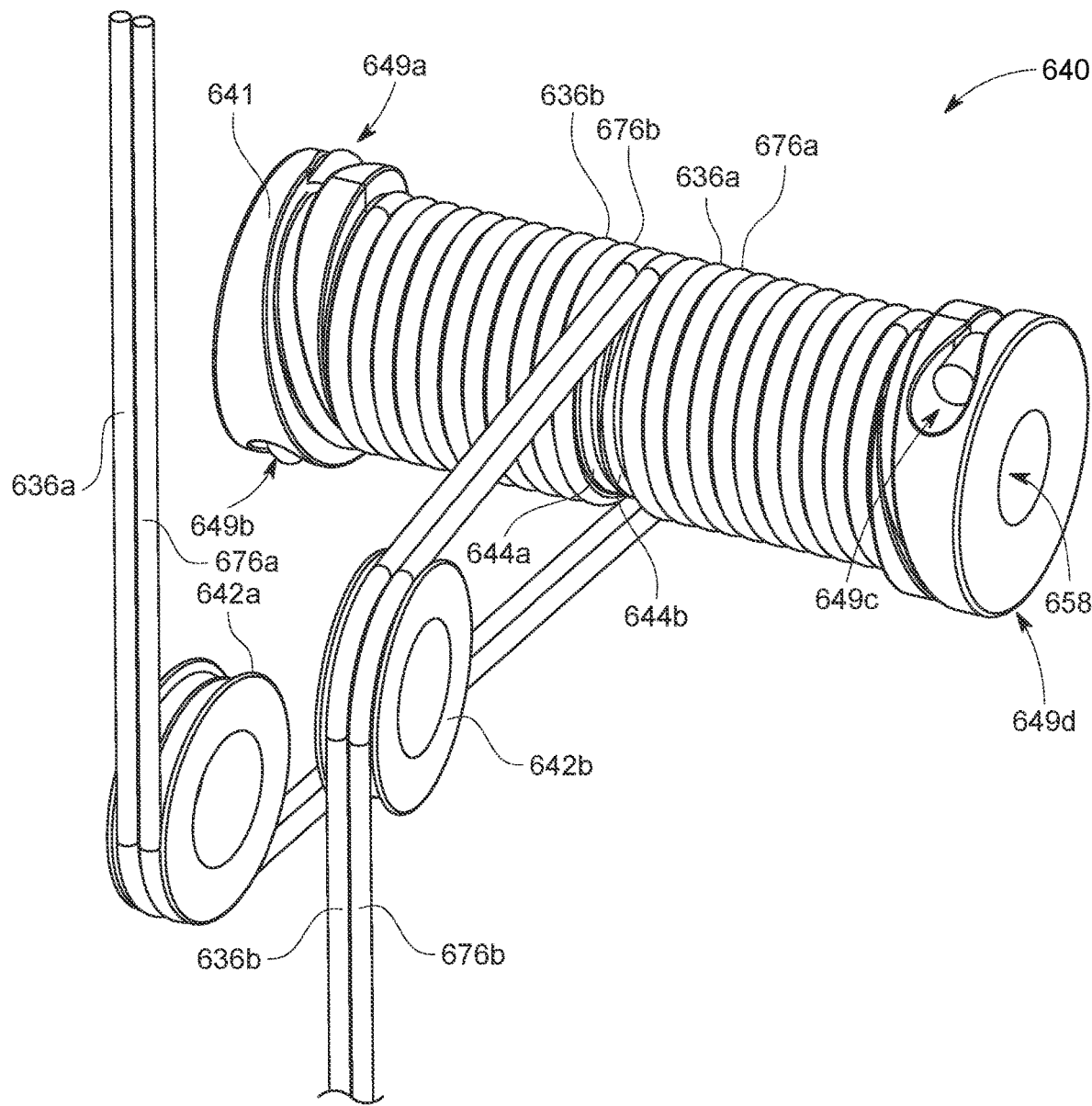
FIG. 8A is a perspective view of a capstan mechanism of the embodiment of the cable-driven prismatic joint of FIG. 6.

FIG. 8A illustrates an embodiment of traveling capstan mechanism 640 (also referred to as capstan mechanism 640 or mechanism 640) designed to spool both the primary cables 636 and the backup cables 676. The traveling capstan mechanism 640 comprises a capstan 641 and take-up pulleys 642 (e.g., take-up pulleys 642a and 642b). The traveling capstan mechanism 640 also has additional components which are similar to components of the capstan mechanisms 440 and 540, and the principle of operation of the mechanism 640 may be similar to that of the mechanisms 440 and 540, except as noted otherwise below. In particular, the traveling capstan mechanism 640 comprises a guide element (not illustrated) engaged with one of the grooves 644a, 644b, which may be configured similarly to the guide roller 446 or 546. Furthermore, in some embodiments the traveling capstan mechanism 640 comprises a spline mechanism (not illustrated) similar to the spline mechanism 460 or 560 to allow translation of the capstan 641, and a drive element similar to the drive element 445 or 545 to drive rotation of the capstan 641. In other embodiments, the capstan 641 is translationally fixed and the take-up pulleys 642 translate, as described above. Some of these components of the traveling capstan mechanism 640 which are similar to components of the mechanisms 440/540 are omitted from FIG. 8A to improve visibility, and duplicative description of these similar components and their principles of operation is also omitted.

The mechanism 640 comprises take-up pulleys 642a, 642b, which are similar to the take-up pulleys 442 or 542 except that the take-up pulleys 642a, 642b may have two grooves to receive both primary cables 636 and backup cables 676. In FIG. 8A, the take-up pulleys 642a, 642b are depicted as being further away from the capstan 641 in order to improve visibility of other components in the Figure, but in practice the take-up pulleys 642a, 642b may be positioned differently. For example, the take-up pulleys 642a, 642b may be arranged in the same manner as the take-up pulleys 442a, 442b, respectively, or in the same manner as the take-up pulleys 542a, 542b, respectively. Although in this example a single take-up pulley 642 supports routing of two cables 636, 676, in other examples each primary cable and each backup cable may have its own separate take-up pulley.

Figure 8B:
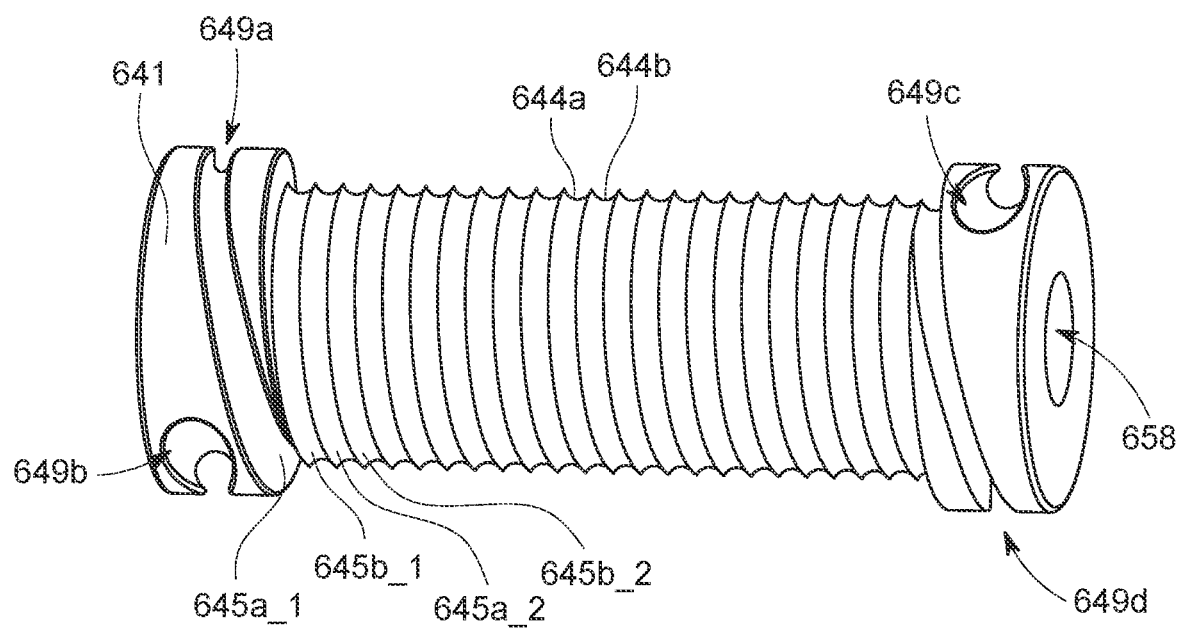
FIG. 8B is a perspective view of the capstan of the capstan mechanism of FIG. 8A shown in isolation.

The traveling capstan mechanism 640 also comprises capstan 641, as shown in FIGS. 8A and 8B. The capstan 641 is similar to the capstan 441 and the capstan 541, except that the capstan 641 comprises two grooves 644a and 644b rather than one groove 444, 544. The two grooves 644a, 644b are arranged in a double-helix configuration, with the grooves 644a, 644b spiraling helically around and along the capstan 641 such that individual windings 645 of the grooves 644a, 644b are interleaved or alternated. The term "winding" in this context refers to a segment of the groove 644a or 644b corresponding to one revolution around the capstan 641. In other words, as shown in FIG. 8B, examined axially along the length of the capstan 641 from left to right, the windings 645 alternate between the grooves 644a, 644b, such that a first winding 645a_1 is part of the groove 644a, a second winding 645b_1 is part of the groove 644b, a third winding 645a_2 is part of the groove 644a, a fourth winding 645b_2 is part of the groove 644b, and so on.

The grooves 644a, 644b can terminate in groove terminals 649 similar to the groove terminals 449 and 549. However, in the capstan 641 there are four groove terminals 649a-649d, two for each groove 644a, 644b. At each end of the capstan 641, two of the groove terminals 649 are arranged on opposite sides of the capstan 641 (i.e., 180 degrees apart around the circumference of the capstan 641) from one another.

Figure 10:
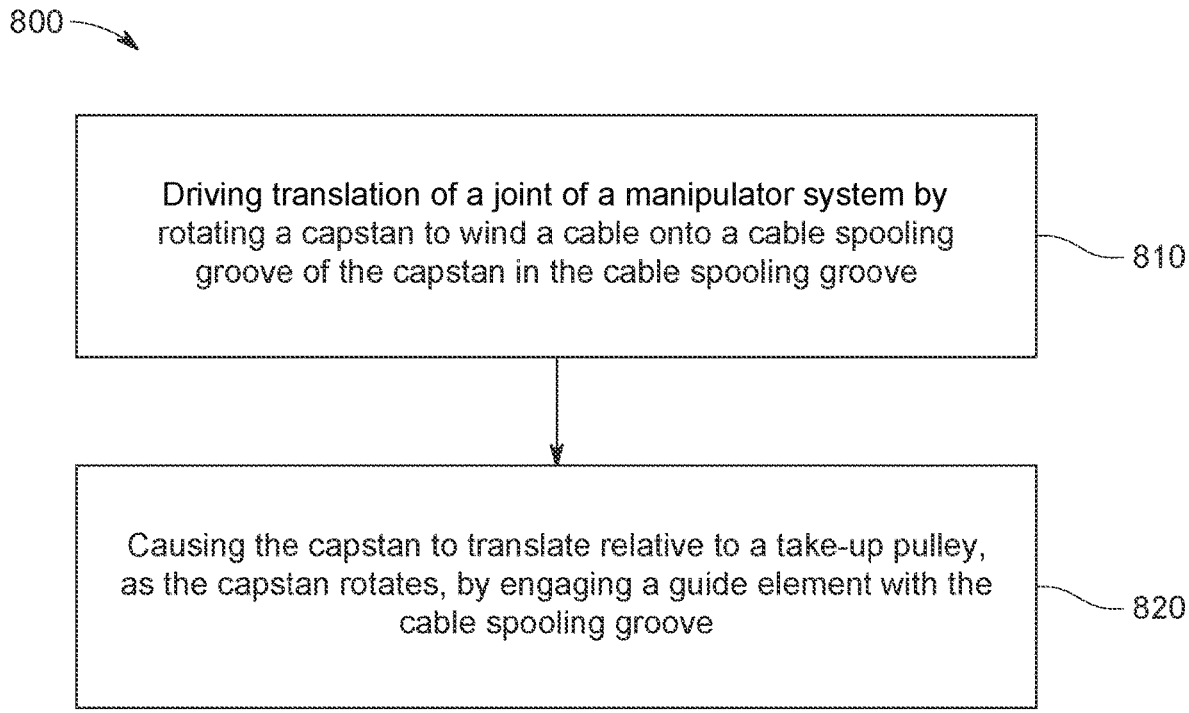
FIG. 10 is a process flow diagram illustrating a method of controlling a traveling capstan.

FIG. 10 illustrates an embodiment of a method 800 of operating a prismatic joint of a manipulator system, such as the prismatic joints 230 or 330. The method 800 may be performed, for example, by a controller of the manipulator system, which may, for example, execute stored machine-readable code comprising instructions to perform the operations of the method. The method 800 may also be performed, for example, by a user of the manipulator system. In some examples, the user may perform the operations by virtue of operating the manipulator system in a manner that causes the operations to be performed, whether or not the user "directly" performs the individual actions. For example, a user may perform the method 800 by virtue of providing an input command at an input device of the manipulator system, wherein the input command is such that it causes the system to perform the operations.

The method 800 comprises driving translation of a joint of a manipulator system by rotating a capstan to wind a cable onto a cable spooling groove of the capstan (block 810). The joint may be any cable driven joint, such as, for example the joints 230 or 330. The capstan may be any capstan that has a cable spooling groove to wind cable, for example, one of the capstans 341, 441, 541, or 641. Rotating the capstan may comprise operating a drive element, such as a motor, to impart torque to a drive shaft coupled to the capstan. In some embodiments, the drive shaft may be a spline drive shaft that allows the capstan to translate axially along the shaft. In other embodiments, the drive shaft does not allow axial translation of the capstan along the shaft. The drive element may be any device that can impart torque and rotary motion to the drive shaft, such as one of the drive elements 345, 445, or 545. The cable may be attached to a movable element of the joint, such as the carriage base 232, 332, such that the winding of the cable onto the capstan pulls the movable element along a path, thereby driving movement of the joint.

The method 800 may further comprise causing the capstan to translate relative to a take-up pulley, which routes the cable onto and off from the capstan, as the capstan rotates by engaging a guide element with the cable spooling groove (block 820). In some embodiments, the guide element is a guide roller, and engaging the guide element with the cable spooling groove includes rolling the guide roller along a surface of the capstan in the cable spooling groove. In such embodiments, the guide roller may be any rotatable element having a generally wheel- or disk-like shape with a circumferential rolling surface having a generally round (e.g., circular) profile in cross section, where the circumferential rolling surface is sized and shaped such that the guide roller can be at least partially received within the cable spooling groove between raised portions of the cable spooling groove. For example, the guide roller may be one of the guide rollers 446 or 546. In some examples, because the guide roller is engaged with the cable spooling groove, rotation of the capstan will automatically cause the guide roller to roll along the surface of the capstan in the cable spooling groove, due to friction. The rolling of the guide roller is not necessarily continuous—for example, due to inevitable tolerances, the guide roller may occasionally lose contact with the capstan and cease rolling for a short moment, and then resume rolling when coming back into contact with the capstan again. In other embodiments, the guide element does not roll or rotate. The engagement of the guide element (whether rolling or not) in the cable spooling groove causes the lateral surfaces of the cable spooling groove and the lateral surfaces of the guide element to push against one another, since the cable spooling groove spirals axially down a length of the capstan. Because the guide element is held axially stationary relative to the take-up pulleys while relative translation between the capstan and the take-up pulleys occurs, this pushing of the guide element against the groove causes the capstan and the take-up pulleys to translate relative to one another. In some embodiments, the capstan can translation axially along its drive shaft and the guide element and the take-up pulley are held translationally stationary relative to the drive shaft, and thus in such embodiments the relative movement of the capstan and the take-up pulleys comprises the capstan translating axially along its shaft. The capstan may be allowed to translate along its drive shaft by virtue of a ball spline mechanism, such as one of the ball spine mechanism 460 or 560. In other embodiments, the capstan is translationally stationary relative to a reference point (e.g., its drive shaft) and the guide element and the take-up pulley are allowed to translate relative to the reference point, and thus in such embodiments the relative movement of the capstan and the take-up pulleys comprises the take-up pulley translating axially relative to the capstan. The guide element and take-up pulley may be allowed to translate by virtue of being coupled to a support structure that is translatable relative to the capstan.

It should be noted that the operations of blocks 810 and 820 are described herein separately, but this does not imply that they are causally independent operations or that they are performed in any particular sequence of performance. In some embodiments, the operations of blocks 810 and 820 may be performed simultaneously, and in some examples, the operations of blocks 810 and 820 may result from, be caused by, or be integral parts of the same underlying action or collection of causally related actions. For example, the action of rotating the capstan (e.g., via rotation of a drive element) may result in the operations of both blocks 810 and block 820 being performed simultaneously.

Figure 11:
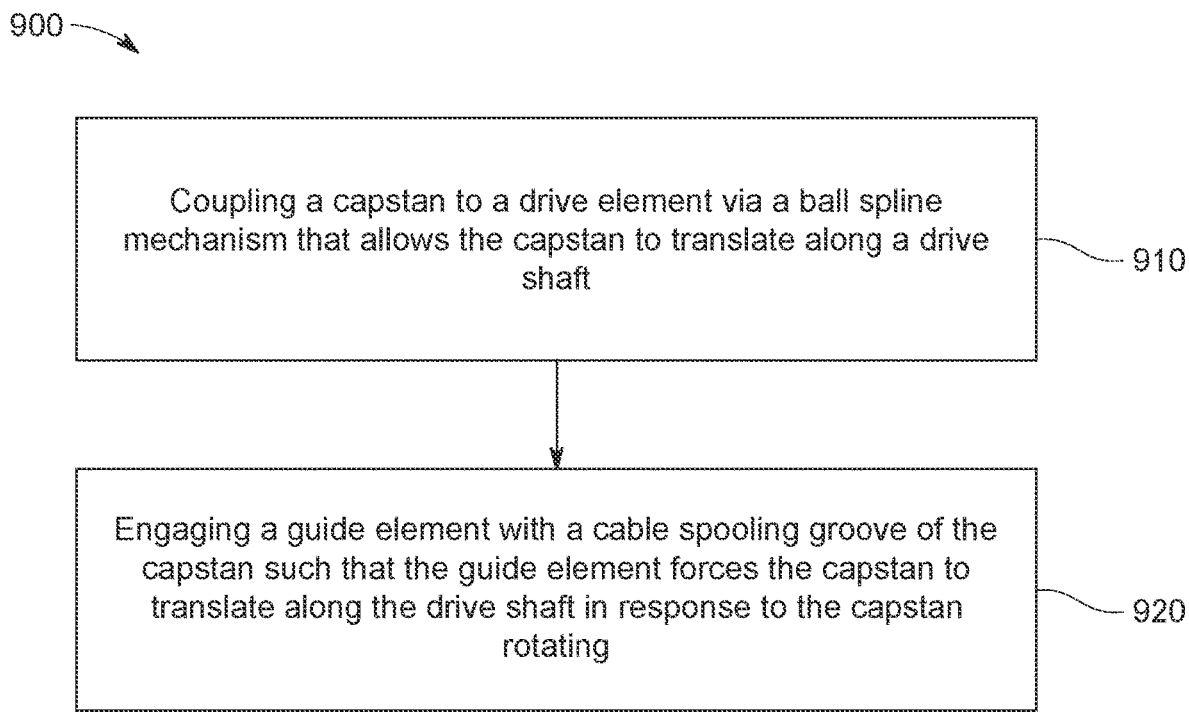
FIG. 11 is a process flow diagram illustrating a method of manufacturing a traveling capstan.

FIG. 11 illustrates an embodiment of method 900 of manufacturing a cable-driven joint of a manipulator system, such as the prismatic joints 230 or 330. The method 900 comprises coupling a capstan to a drive element via a ball spline mechanism that allows the capstan to translate along a drive shaft (block 910). The capstan may be, for example, one of the capstans 341, 441, 541, or 641. The drive element may be any device that can impart torque and rotary motion to a drive shaft, such as one of the drive elements 345, 445, or 545. The ball spline mechanism may be any ball spline mechanism that can drive rotation of the capstan while also allowing the capstan to translate along the shaft driving the rotation, such as one of the ball spine mechanism 460 or 560.

The method 900 further comprises engaging a guide element with a cable spooling groove of the capstan such that the guide element forces the capstan to translate axially along the drive shaft in response to rotation of the capstan (block 920). The guide element may be any rigid structure that is capable of engaging with the cable spooling groove of the capstan, including a rotatable element (guide roller) or a non-rotatable element. For example, the guide element may be one of the guide rollers 446 or 546. Engaging the guide element with the cable spooling groove may comprise coupling the guide element to a support structure and coupling the capstan to the support structure such that a surface of the guide element is at least partially received within the cable spooling groove. The guide element and the capstan may be coupled to the support structure simultaneously, or in any order. In examples in which the guide element is a rotatable guide roller, the guide roller is coupled to the support structure by a rotational bearing, such that the guide roller is held axially stationary relative to the support structure. The capstan is coupled to the support structure (directly or indirectly via intermediate components) by the drive shaft, which is axially stationary relative to the support structure. In some examples, engaging a guide roller with the cable spooling groove may further comprise tilting the rotational axis of the guide roller so that the rotational axis of the guide roller is not parallel to the rotational axis of the capstan. In some examples, the tilting of the rotational axis of the guide roller may be such that the guide roller is aligned with the angle of ascent of the cable spiraling groove. In other words, the angle between the normal plane of the guide roller and the normal plane of the capstan is equal to the angle of ascent of the groove. In some examples, coupling the guide roller to the support structure may comprise locating the guide roller such that it occupies a region of space between two take-up pulleys coupled do the support structure and between the take-up pulleys and the capstan.

Figure 12A:
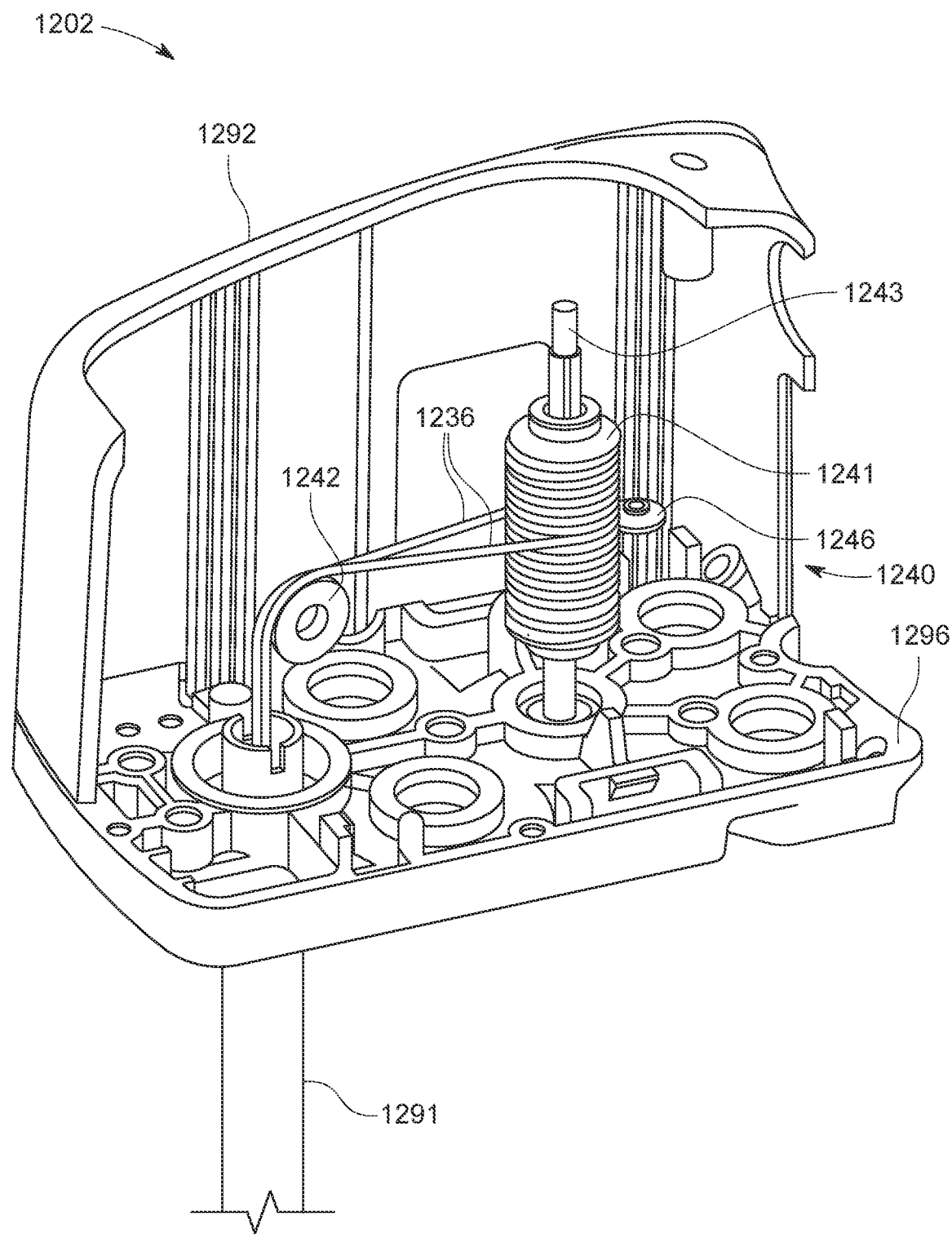
FIG. 12A. is a cutaway perspective view of the embodiment of an instrument comprising a traveling capstan mechanism.
Figure 12B:
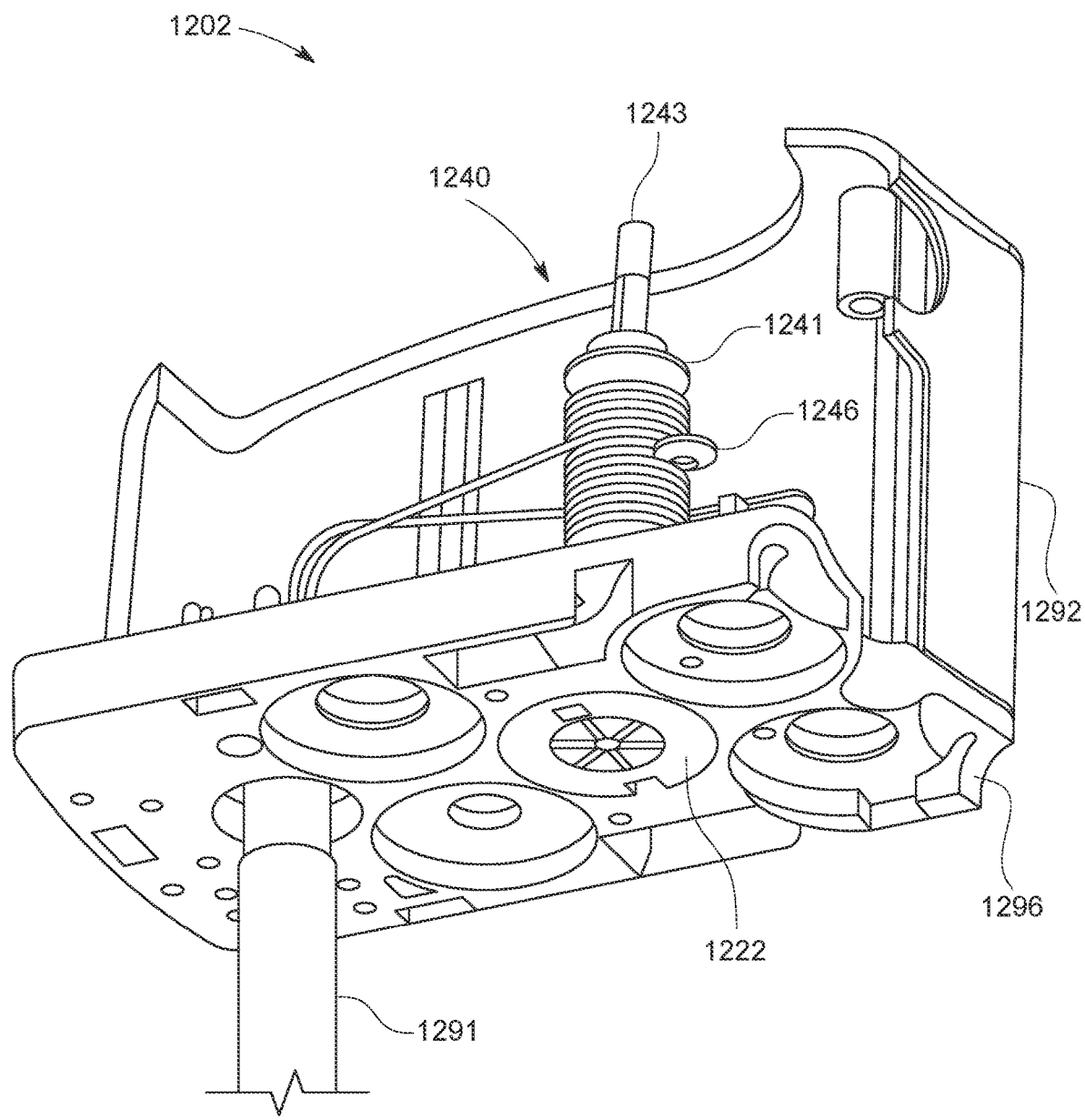
FIG. 12B is another cutaway perspective view of the instrument of FIG. 12B.

FIGS. 12A and 12B illustrate an embodiment of an instrument 1202 that comprises a cable drive system that utilizes a traveling capstan mechanism. The instrument 1202 may be used as the instrument 202 or 102. In some embodiments, the instrument 1202 is a medical instrument, such as a surgical instrument. In other embodiments, the instrument 1202 is a non-medical (e.g., industrial) instrument.

The instrument 1202 comprises an instrument transmission housing 1292, a shaft 1291 coupled to the instrument transmission housing 1292, and an end effector (not illustrated) attached to a distal end portion of the shaft 1291. Optionally, in some embodiments, the shaft 1291 may be coupled to a proximal end portion of the instrument transmission housing 1292. The end effector may be configured to perform one or more operations, such as grasping, cutting, delivering flux, stapling, etc. Any type of end effector that is desired may be used. Various end effectors are familiar to those of ordinary skill in the art, and thus the end effector is not illustrated or described in detail herein. In some embodiments, the end effector or some other part of the instrument may also be moveable relative to the shaft 1291, for example via a wrist mechanism (not illustrated).

The instrument transmission housing 1292 comprises an interface portion 1296 that is configured to couple the instrument 1202 to a manipulator. For example, in some embodiments the interface portion 1296 is configured to couple the instrument 1202 to an instrument carriage, such as the instrument carriage 220 described above. The instrument transmission housing 1292 also comprises drive inputs 1222 that interface with and are driven by drive outputs of the manipulator, such as the drive outputs 222 of the instrument carriage 220. The drive inputs 1222 may directly interface with the drive outputs of the manipulator or they may interface with the drive outputs of the manipulator via an intermediary such as an ISA. The ISA may be placed between the interface portion 1296 and the instrument carriage 220 to maintain sterile separation between the instrument 1202 and the manipulator. In FIGS. 12A and 12B, only one drive input 1222 is illustrated, but in practice additional drive inputs 1222 of a variety of types could also be included in the interface portion 1296.

The instrument transmission housing 1292 also comprises a force transfer mechanism to convert the motion of the drive inputs 1222, driven by an actuator of a control mechanism (e.g., from the drive outputs of the manipulator), into motion that drives degrees of freedom of the instrument 1202 and/or actuates a function of the end effector. Specifically, in the embodiment of FIGS. 12A and 12B, the force transfer mechanism includes traveling capstan mechanism 1240 comprising a capstan 1241, a drive shaft 1243, a guide element 1246, and one or more take-up pulleys 1242. The traveling capstan mechanism 1240 may be similar to any of the traveling capstan mechanisms 340, 440, 540, and 640 described above, with various modifications as described below and as would be apparent to one of ordinary skill in the art. The traveling capstan mechanism 1240 comprises a capstan 1241. The capstan 1241 may be similar to any one of the capstans 341, 441, 541, and 641 described above, and comprises one or more grooves spiraling helically round the capstan to spool cables 1236 on and off the capstan 1241 as the capstan 1241 rotates. In the traveling capstan mechanism 1240, the drive shaft 1243 is coupled to and driven to rotate by the drive input 1222. Cables 1236 that extend through the shaft 1291 are routed to and from the capstan 1241 via take-up pulleys 1242. The traveling capstan mechanism 1240 is configured to provide relative translation between the take-up pulleys 1242 and the capstan 1241 in response to rotation of the capstan 1241. Specifically, the capstan mechanism 1240 comprises a guide element 1246 to engage with the groove in the capstan 1241 and thereby cause the relative translation between the capstan 1241 and the take-up pulleys 1242 as the capstan 1241 rotates. The guide element 1246 is translationally fixed relative to the take-up pulleys 1242 while there is relative translation between the guide element 1246 and the capstan 1241. Thus, interaction between the guide element 1246 and the walls of the groove in the capstan 1241 as the capstan 1241 rotates forces the relative translation between the capstan 1241 and the take-up pulleys 1242. The take-up pulleys 1242 and the guide element 1246 may be coupled to and supported by support structures (not illustrated).

In the illustrated embodiment, the relative translation of the capstan 1241 and the take-up pulleys 1242 comprises the capstan 1241 translating relative to the instrument transmission housing 1292 while the take-up pulleys 1242 remain translationally stationary relative to the instrument transmission housing 1292. Specifically, in the illustrated embodiment, the take-up pulleys 1242 and the guide element 1246 are both coupled to and translationally stationary relative to the instrument transmission housing 1292, and therefore the interaction of the guide element 1246 with the capstan 1241 forces the capstan to translate relative to the instrument transmission housing 1292. In the illustrated embodiment, the drive shaft 1243 is a spline drive shaft that drives rotation of the capstan 1241 while allowing the capstan 1241 to translate axially along the drive shaft 1243. Any of the drive shaft mechanisms described above may be used to provide translation for the capstan 1241.

In other embodiments, the take-up pulleys 1242 may translate relative to the instrument transmission housing 1292 while the capstan 1241 is translationally stationary relative to the instrument transmission housing 1292. For example, a support structure (not illustrated) may be coupled to the take-up pulleys 1242 and the guide element 1246 and the support structure may be translatable relative to the instrument transmission housing 1292.

The cables 1236 may control a degree of freedom of movement of the instrument 1202 and/or actuate a function of the instrument 1202. For example, the cables 1236 may be moved by the capstan mechanism 1240 to cause movement of an element of the instrument 1202, such as translation of a cutting blade of the end effector or movement (e.g., telescoping) of a portion of the shaft, and/or articulation of a wrist or the end effector.

It is to be understood that both the general description and the detailed description provide example embodiments that are explanatory in nature and are intended to provide an understanding of the present disclosure without limiting the scope of the present disclosure. Various mechanical, compositional, structural, electrical, and operational changes may be made without departing from the spirit and scope of this description and the claims. In some instances, well-known circuits, structures, and techniques have not been shown or described in detail in order not to obscure the embodiments. Like numbers in two or more figures represent the same or similar elements.

Further, the terminology used herein to describe aspects of the invention, such as spatial and relational terms, is chosen to aid the reader in understanding example embodiments of the invention but is not intended to limit the invention. For example, spatially terms-such as "beneath", "below", "lower", "above", "upper", "proximal", "distal", "up", "down", and the like—may be used herein to describe directions or one element's or feature's spatial relationship to another element or feature as illustrated in the figures. These spatial terms are used relative to the figures and are not limited to a particular reference frame in the real world. Thus, for example, the direction "up" in the figures does not necessarily have to correspond to an "up" in a world reference frame (e.g., away from the Earth's surface). Furthermore, if a different reference frame is considered than the one illustrated in the figures, then the spatial terms used herein may need to be interpreted differently in that different reference frame. For example, the direction referred to as "up" in relation to one of the figures may correspond to a direction that is called "down" in relation to a different reference frame that is rotated 180 degrees from the figure's reference frame. As another example, if a device is turned over 180 degrees in a world reference frame as compared to how it was illustrated in the figures, then an item described herein as being "above" or "over" a second item in relation to the Figures would be "below" or "beneath" the second item in relation to the world reference frame. Thus, the same spatial relationship or direction can be described using different spatial terms depending on which reference frame is being considered. Moreover, the poses of items illustrated in the figure are chosen for convenience of illustration and description, but in an implementation in practice the items may be posed differently.

In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components, unless specifically noted otherwise. Mathematical and geometric terms are not necessarily intended to be used in accordance with their strict definitions unless the context of the description indicates otherwise, because a person having ordinary skill in the art would understand that, for example, a substantially similar element that functions in a substantially similar way could easily fall within the scope of a descriptive term even though the term also has a strict definition.

Elements and their associated aspects that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

As used herein, "proximal" and "distal" are spatial/directional terms that describe locations or directions based on their relationship to the two ends of a kinematic chain. "Proximal" is associated with the end of the kinematic chain that is closer to the base or support of the chain, while "distal" is associated with the opposite end of the kinematic chain, which often comprises an end effector of an instrument. Thus, a "proximal" location is a location that is relatively closer to the base of the kinematic chain. For example, the "proximal end portion" of a link refers to the portion of the link that is closer to the base of the kinematic chain than the rest of the link. Conversely, a "distal" location is a location that is relatively farther from the base of the kinematic chain. For example, the "distal end portion" of a link refers to the portion of the link that is farther from the base of the kinematic chain than the rest of the link. The terms closer and farther as used above refer to proximity along the kinematic chain, rather than absolute distance. "Proximal" and "distal" directions are directions that point generally towards a proximal location or distal location, respectively. For example, each link could be described as having associated proximal and distal directions, with the proximal direction of a link pointing generally from around its distal end to around its proximal end and with the distal direction pointing generally from around its proximal end to somewhere around its distal end. It should be understood that for a given kinematic chain there may be many different directions that could be described as "proximal" or "distal" depending on the context, as there may be many links and many possible poses for those links. For example, a "distal" direction described in relation to one link may point diagonally downward relative to a world reference frame, while a "distal" direction described in relation to another link that is at an angle to the first link may point diagonally upward relative to the world reference frame. Moreover, if the poses of the links change, the proximal and distal directions associated with the links may change. Thus, there is no single "proximal" or "distal" direction, but rather many possible "proximal" or "distal" directions, depending on the context. In the context of an instrument attached to the manipulator, "proximal" refers to the end of the instrument attached to the manipulator, while "distal" refers to the opposite end of the instrument which has an end effector. In the context of a surgical procedure, the "distal" end of the kinematic chain is the end that is inserted into a patient, and thus "distal" may also be used to refer to a location that is closer to a patient or to a direction of insertion into a patient, whereas a "proximal" may refer to a location that is further from to the patient or a direction of removal from the patient.

What is claimed is:

1. A capstan mechanism, comprising:
a capstan comprising an outer surface;
a groove in the outer surface of the capstan, the groove configured to receive and guide a cable to spool onto the capstan as the capstan rotates;
a take-up pulley to route the cable onto and off from the capstan; and
a guide element engaged with the groove, the guide element causing relative translation between the capstan and the take-up pulley in response to rotation of the capstan.

2. The capstan mechanism of claim 1, wherein:
the relative translation between the capstan and the take-up pulley comprises the capstan translating relative to a drive shaft that drives rotation of the capstan while the take-up pulley is translationally stationary relative to the drive shaft.

3. The capstan mechanism of claim 2, further comprising:
a support structure that is translationally stationary relative to the drive shaft, wherein the guide element and the take-up pulley are coupled to and translationally stationary relative to the support structure and the capstan is translationally movable relative to the support structure.

4. The capstan mechanism of claim 3, wherein:
the guide element is a guide roller that is rotatably coupled to the support structure and configured to roll along the groove.

5. The capstan mechanism of claim 4, wherein:
the capstan has a capstan axis of rotation,
the guide roller has a guide roller axis of rotation, and
the guide roller axis of rotation is nonparallel to the capstan axis of rotation.

6. The capstan mechanism of claim 4, wherein:
the groove spirals helically around the capstan at a helix angle relative to a normal plane of the capstan, the normal plane of the capstan being perpendicular to the capstan axis of rotation, and
an angle between a normal plane of the guide roller and the normal plane of the capstan is equal to the helix angle of the groove, the normal plane of the guide roller being perpendicular to a guide roller axis of rotation.

7. The capstan mechanism of claim 2, further comprising:
a ball spline mechanism comprising the drive shaft and ball bearings positioned between the drive shaft and the capstan,
wherein the drive shaft is a spline drive shaft and rotation of the spline drive shaft causes rotation of the capstan and the capstan is translationally movable relative to the spline drive shaft.

8. The capstan mechanism of claim 7, wherein:
the ball spline mechanism comprises a first groove in the spline drive shaft, a second groove in a radially-inward facing surface of a bore of the capstan, and a tube between the spline drive shaft and the capstan configured to hold the ball bearings, the ball bearings being engaged with the first and second grooves.

9. The capstan mechanism of claim 7, wherein:
the ball spline mechanism comprises a recirculating ball spline unit coupled to the capstan and slidably coupled to the spline drive shaft.

10. The capstan mechanism of claim 1, wherein:
the groove is a first groove spiraling helically around the outer surface of the capstan and the capstan mechanism further comprises a second groove spiraling helically around the outer surface of the capstan.

11. The capstan mechanism of claim 10, further comprising:
one or more first cables, each wound onto the capstan in at least a portion of the first groove; and
one or more second cables each wound onto the capstan in at least a portion of the second groove.

12. The capstan mechanism of claim 11, wherein:
the one or more second cables are configured to experience less stress than the one or more first cables.

13. The capstan mechanism of claim 12, wherein:
the one or more second cables have a lower elastic modulus than the one or more first cables.

14. The capstan mechanism of claim 1, wherein:
the relative translation between the capstan and the take-up pulley comprises the take-up pulley translating relative to a drive shaft that drives rotation of the capstan while the capstan is translationally stationary relative to the drive shaft.

15. The capstan mechanism of claim 14, further comprising:
a support structure, wherein the guide element and the take-up pulley are coupled to and translationally stationary relative to the support structure and the support structure is translationally movable relative to the capstan.

16. The capstan mechanism of claim 1, wherein:
the groove spirals helically around the outer surface of the capstan.

17. A manipulator system for supporting and remotely actuating instruments, comprising:
a manipulator comprising a first link, an instrument carriage, and a joint coupling the instrument carriage relative to the first link, wherein:
the instrument carriage is configured to support an instrument;
the joint comprises:
a capstan mechanism;
one or more cables coupled to the instrument carriage; and
one or more pulleys routing the cables between the instrument carriage and the capstan mechanism, wherein the capstan mechanism comprises:
a capstan comprising an outer surface;
a groove in the outer surface of the capstan, the groove configured to receive and guide a cable to spool onto the capstan as the capstan rotates;
one or more take-up pulleys to route the one or more cable onto and off from the capstan; and
a guide element engaged with the groove, the guide element causing relative translation between the capstan and the one or more take-up pulleys in response to rotation of the capstan.

18. The manipulator system of claim 17, wherein:
the relative translation between the capstan and the one or more take-up pulleys comprises the capstan translating relative to a drive shaft that drives rotation of the capstan while the one or more take-up pulleys are translationally stationary relative to the drive shaft.

19. The manipulator system of claim 18, further comprising:
a ball spline mechanism comprising the drive shaft and ball bearings between the drive shaft and the capstan, wherein the drive shaft is a spline drive shaft, rotation of the spline drive shaft causes rotation of the capstan, and the capstan is translationally movable relative to the spline drive shaft.

20. The manipulator system of claim 17, wherein:
the groove is a first groove spiraling helically around the outer surface of the capstan and the capstan mechanism further comprises a second groove spiraling helically around the outer surface of the capstan.

21. The manipulator system of claim 20, wherein the cables comprise:
one or more first cables, each wound onto the capstan in a portion of the first groove, and
one or more second cables, each wound onto the capstan in a portion of the second groove.

22. The manipulator system of claim 21, wherein:
the second cables are configured to experience less stress than the first cables.

23. The manipulator system of claim 22, wherein:
one or more springs, each coupled in series with a corresponding one of the second cables.

24. The manipulator system of claim 17, further comprising:
a track coupled to the first link; and
a carriage base movably coupled to the track and coupled to the instrument carriage, the one or more cables coupled to the carriage base to move the carriage base along the track.

\* \* \* \* \*